(12) United States Patent
Jung et al.

(10) Patent No.: US 11,198,859 B2
(45) Date of Patent: Dec. 14, 2021

(54) RECOMBINANT POLYNUCLEOTIDE CODING FOR POLYPEPTIDE COMPRISING REPORTER MOIETY, SUBSTRATE MOIETY AND DESTABILIZING MOIETY, HOST CELL COMPRISING SAME AND USE OF SAME

(71) Applicant: Medytox Inc., Chungcheongbuk-do (KR)

(72) Inventors: Hyun Ho Jung, Seoul (KR); Gi Hyeok Yang, Chungcheongnam-do (KR); Jun Ho Lee, Gyeonggi-do (KR); Dong Kyu Lee, Chungcheongbuk-do (KR); Young Rae Lee, Chungcheongbuk-do (KR)

(73) Assignee: MEDYTOX INC., Chungcheongbuk-Do (KR)

( * ) Notice: Subject to any disclaimer, the term of this patent is extended or adjusted under 35 U.S.C. 154(b) by 517 days.

(21) Appl. No.: 16/098,278

(22) PCT Filed: May 24, 2017

(86) PCT No.: PCT/KR2017/005420
§ 371 (c)(1),
(2) Date: Nov. 1, 2018

(87) PCT Pub. No.: WO2017/204561
PCT Pub. Date: Nov. 30, 2017

(65) Prior Publication Data
US 2019/0161745 A1 May 30, 2019

(30) Foreign Application Priority Data
May 4, 2016 (KR) ........................ 10-2016-0063722

(51) Int. Cl.
| | | |
|---|---|---|
| *C12N 15/62* | (2006.01) | |
| *C12N 9/52* | (2006.01) | |
| *C12N 5/0793* | (2010.01) | |
| *G01N 33/50* | (2006.01) | |
| *C07K 14/005* | (2006.01) | |
| *C07K 14/435* | (2006.01) | |
| *C12N 9/02* | (2006.01) | |

(52) U.S. Cl.
CPC .............. *C12N 9/52* (2013.01); *C07K 14/005* (2013.01); *C07K 14/43595* (2013.01); *C12N 5/0619* (2013.01); *C12N 9/0069* (2013.01); *C12Y 113/12007* (2013.01); *C12Y 304/24069* (2013.01); *G01N 33/5058* (2013.01); *C07K 2319/033* (2013.01); *C07K 2319/50* (2013.01); *C12N 2770/32031* (2013.01)

(58) Field of Classification Search
CPC ................ C07K 2319/60; C12N 15/62; C12Y 133/12007
See application file for complete search history.

(56) References Cited

U.S. PATENT DOCUMENTS

| | | |
|---|---|---|
| 8,940,482 B1 | 1/2015 | Oyler et al. |
| 2004/0002056 A1 | 1/2004 | Lorens et al. |
| 2004/0146987 A1* | 7/2004 | Zdanovsky ............ C12N 15/67 435/69.7 |
| 2011/0143362 A1* | 6/2011 | Oyler .................. C12N 15/1086 435/6.18 |
| 2015/0044709 A1 | 2/2015 | Eisele |
| 2015/0159193 A1 | 6/2015 | Tucker et al. |
| 2016/0069862 A1 | 3/2016 | Tucker et al. |
| 2016/0289731 A1 | 10/2016 | Eisele et al. |

FOREIGN PATENT DOCUMENTS

| | | |
|---|---|---|
| WO | 2003065012 A2 | 8/2003 |
| WO | 2011071956 A2 | 6/2011 |
| WO | 2012047325 A2 | 4/2012 |
| WO | 2012166943 A1 | 12/2012 |

OTHER PUBLICATIONS

Djakovic et al. 2009; Regulation of the proteasome by neuronal activity and calcium/calmodulin-dependent protein kinase II. Journal of Biological Chemistry. 284(390: 26655-26665.*
Mateus et al. 2000; Destabilized green fluorescent protein for monitoring dynamic changes in yeast gene expression with flow cytometry. Yeast. 16: 1313-1323.*
Li et al. 1998; Generation of destabilized green fluorescent protein as a transcription reporter. Journal of Biological Chemistry. 273(52): 34970-34975.*
Corish et al. 1999; Attenuation of green fluorescent protein half-life in mammalian cells. Protein Engineering. 12(12): 1035-1040.*
Kim et al. 2012: A novel fluorescent reporter system for monitoring and identifying RNase III activity and its target RNAs. RNA Biology. 9(9): 1167-1176.*
European Office Action (Communication Pursuant to Article 94(3) EPC) dated Oct. 16, 2020, issued in European Application No. 17803080.5.
Sainsbury, F. et al., "Multimodal Protein Constructs for Herbivore Insect Control", Toxins, 4:455-475, Basel, Switzerland (2012).
Iwawaki, T. et al., "Transgenic Mouse Model for Imaging of Interleukin-1β-related Inflammation in vivo". Nature, Scientific Reports, 5:17205, pp. 1-10, London (Nov. 24, 2015).
International Search Report for PCT/KR2017/005420, dated Nov. 29, 2017.
Japanese Notice of Reasons of Rejection dated Nov. 12, 2019 in corresponding Japanese Application No. 2018-560622 (with English translation).

(Continued)

*Primary Examiner* — Karen Cochrane Carlson
(74) *Attorney, Agent, or Firm* — Potomac Law Group, PLLC

(57) ABSTRACT

Provided are a recombinant polynucleotide encoding a polypeptide including a reporter moiety, a substrate moiety, and a destabilization moiety, a host cell including the same, and use thereof to measure the level of a protease by using the recombinant polynucleotide.

15 Claims, 10 Drawing Sheets

Specification includes a Sequence Listing.

(56) References Cited

OTHER PUBLICATIONS

Callahan, B.P. et al., "Cut and glow: Protease activation of split green fluorescent protein," Chembiochem, Nov. 2010, vol. 11(16), pp. 1-11, WILEY-VCH Verlag GmbH & Co. KGaA, Weinheim.
Extended European Search Report dated Jul. 18, 2019 for European Application No. 17803080.5.

* cited by examiner

R: REPORTER SEQUENCE
S: SUBSTRATE SEQUENCE
D: DESTABILIZATION SEQUENCE

I: INTERNAL STANDARD SEQUENCE
B: BICISTRONIC EXPRESSION-INDUCING SEQUENCE
R: REPORTER SEQUENCE
S: SUBSTRATE SEQUENCE
D: DESTABILIZATION SEQUENCE

R: REPORTER SEQUENCE : NANO-lUCIFERASE
S: SUBSTRATE SEQUENCE : SNAP25
D: DESTABILIZATION SEQUENCE : CL1-PEST

B

| | BoNT/A 0pM | BoNT/A 10nM |
|---|---|---|
| Nluc | 10390 | 111357 |

I: INTERNAL STANDARD SEQUENCE : FIREFLY-lUCIFERASE
B: BICISTRONIC EXPRESSION-INDUCING SEQUENCE : P2a
R: REPORTER SEQUENCE : NANO-lUCIFERASE
S: SUBSTRATE SEQUENCE : VAMP2
D: DESTABILIZATION SEQUENCE : CL1-PEST

B

BoNT/B LC

| | 0ug/well | 1ug/well |
|---|---|---|
| Nluc/Fluc | 8.79 | 16.76 |

FIG. 11

BoNT/A API

| | 대조군 | 1pM | 10pM | 100pM | 1nM | 10nM |
|---|---|---|---|---|---|---|
| Nluc/Fluc | 2019.3333 | 2521.6667 | 5065 | 15641.667 | 65785.667 | 140494.33 |

FIG. 12

Firefly Luciferase

| | 0U/well | 2U/well | 4U/well | 6U/well | 8U/well | 10U/well |
|---|---|---|---|---|---|---|
| Fluc | 26564 | 20709 | 19314 | 20269 | 24528 | 21236 |

…

RECOMBINANT POLYNUCLEOTIDE CODING FOR POLYPEPTIDE COMPRISING REPORTER MOIETY, SUBSTRATE MOIETY AND DESTABILIZING MOIETY, HOST CELL COMPRISING SAME AND USE OF SAME

REFERENCE TO SEQUENCE LISTING SUBMITTED ELECTRONICALLY

The content of the electronically submitted sequence listing in ASCII text file (Name: 19472_0060001_sequence_ST25.txt; Size: 21 KB; and Date of Creation: Nov. 1, 2018) filed with the application is incorporated herein by reference in its entirety.

TECHNICAL FIELD

The present disclosure relates to a recombinant polynucleotide encoding a polypeptide including a reporter moiety, a substrate moiety, and a destabilization moiety, a host cell including the same, and a method of measuring the level of a protease by using the recombinant polynucleotide using the same.

BACKGROUND ART

Proteases are enzymes that perform proteolysis. Proteases degrade peptide bonds that link amino acids to each other in polypeptide chains by hydrolysis. Proteases may include neurotoxins. *Clostridium botulinum* and *Clostridium tetani* produce very potent neurotoxins, for example, *botulinum* toxin (BoNT) and tetanus toxin (TeNT). These clostridial neurotoxins bind specifically to neuronal cells and inhibit the release of neurotransmitters. Some proteases, such as neurotoxins, not only have very strong toxicity but also are present in very small amounts. Accordingly, there is a need to develop a method of measuring their activity safely and accurately.

An aspect provides a recombinant polynucleotide including a first polynucleotide that encodes a polypeptide that includes: a reporter moiety; a destabilization moiety; and a substrate moiety operatively linking the reporter moiety to the destabilization moiety, wherein the substrate moiety includes a cleavage site of protease activity.

Another aspect provides a host cell containing the recombinant polynucleotide.

Another aspect provides a kit for determining proteolytic activities of a protease polypeptide, the kit including a polypeptide encoded by the recombinant polynucleotide described above, and a detection agent that measures signals emitted by a reporter moiety, an internal standard reporter, or a product thereof.

Another aspect provides a kit for determining proteolytic activities of a protease polypeptide, the kit including a host cell including the recombinant polynucleotide described above, and a detection agent that measures signals emitted by a reporter moiety, an internal standard reporter, or a product thereof.

Another aspect provides a method of determining protease activities of a protease polypeptide in a sample, the method including: contacting a polypeptide encoded by the recombinant polynucleotide with a sample suspected of containing a protease polypeptide; and measuring signals emitted by the reporter moiety or a product thereof in a product obtained by the contacting.

Another aspect provides a method of determining protease activities of a protease polypeptide in a sample, the method including: contacting the host cell with a sample suspected of containing a protease polypeptide; and measuring signals emitted by the reporter moiety, the internal standard reporter, or a product thereof in a product obtained by the contacting.

Another aspect provides a method of determining characteristics of protease polypeptide in a sample, the method including contacting a polypeptide encoded by the recombinant polynucleotide with the protease polypeptide; measuring signals emitted by the reporter moiety or product thereof in a product obtained by the contacting; and determining, based on measured signals, one or more selected from an onset time of emission of the signals and a duration thereof.

Another aspect provides a method of determining characteristics of protease polypeptide in a sample, the method including contacting the host cell with the protease polypeptide; measuring signals emitted by a reporter moiety, an internal standard reporter, or a product thereof in a product obtained by the contacting; and determining, based on measured signals, one or more selected from an onset time of emission of the signals and a duration thereof.

TECHNICAL SOLUTION

A first aspect provides a recombinant polynucleotide including a first polynucleotide that encodes a polypeptide that includes: a reporter moiety, a destabilization moiety; and a substrate moiety operatively linking the reporter moiety to the destabilization moiety, wherein the substrate moiety includes a cleavage site of protease activity.

Regarding the recombinant polynucleotide, the reporter moiety may be a material that emits a detectable signal or releases a material that emits a detectable signal in a reaction catalyzed thereby (hereinafter also referred to as "product"). The reporter moiety may be selected from a fluorescence protein, β-lactamase, β-galactosidase, alkaline phosphatase, chloramphenicol acetyltransferase, β-glucouronidase, peroxidase, and luciferase. The fluorescence protein may be selected from GFP, YFP, Citrine, CFP, RFP, Kaede, PA-GFP, Emerald, Venus, DsRed, mHoneydew, mBanana, mOrange, tdTomato, mTangerine, mStrawberry, mCherry, mRasberry, mPlum, ZsGreen, and ZsYellow protein.

Regarding the recombinant polynucleotide, the destabilization moiety may be characterized in reducing the intracellular expression of the first polynucleotide in cells compared to when the destabilization moiety is absent. The expression may be an expression at an mRNA level or a protein level. The destabilization moiety may promote the degradation of mRNA or protein intracellularly expressed by the first polynucleotide in cells. The destabilization moiety may be PEST, CL1, or a fusion protein of PEST and CL1.

The protease may be originated from bacteria. The bacteria may be of the *Clostridium* genus. The protease may be a neurotoxin polypeptide. The protease may be an endoprotease. The neurotoxin polypeptide may be a *botulinum* toxin serotype A (BoNT/A), BoNT/B, BoNT/C, BoNT/D, BoNT/CD, BoNT/DC, BoNT/E, BoNT/F, BoNT/FA, BoNT/G, tetanus neurotoxin (TeNT), or a mutant thereof. The protease may cleave a cleavage site in the substrate moiety. The cleavage site may be a site recognized and cleaved by the protease. An amino acid sequence of each of these *botulinum* toxin serotypes and a polynucleotide encoding the amino acid sequence are known. The amino acid sequence of each of these *botulinum* toxin serotypes and the polynucleotide encoding the amino acid sequence may be, for example, those having the sequences of SEQ ID NOS: 1-14 disclosed in WO2004-031355.

The cleavage site may be a peptide substrate that may be cleaved at a specific cleavage site by a protease. The cleavage site may be, for example, a cleavage site that is recognized and cleaved by endogenous proteases of neurotoxin. The cleavage site of neurotoxin may be naturally occurring or artificially created. The cleavage site of neurotoxin may be derived from a protein that is recognized and cleaved by, for example, BoNT/A protease, BoNT/E protease, or mutants thereof. The protein may be SNAP-25, an isoform thereof, a paralogue, or an ortholog. SNAP-25 may be derived from a human, a rat, a mouse, bovine, danio, carassius, xenopus, torpedo, strongylocentrotus, loligo, lymnaea, or aplysia. SNAP-25 may be SNAP-25A or SNAP-25B.

In one embodiment, the cleavage site of neurotoxin may be derived from a protein that is recognized and cleaved by, for example, BoNT/B protease, BoNT/D protease, BoNT/F protease, BoNT/G protease, or mutants thereof. The protein may be VAMP, an isoform thereof, a paralogue, or an ortholog. The protein VAMP, an isoform thereof, a paralogue, or an ortholog may be, for example, human or mouse VAMP-1, VAMP-2, VAMP-3/cellubravin, bovine VAMP-2, rat VAMP-2, or VAMP-3, chicken VAMP-1, VAMP-2, or VAMP-3, Torpedo VAMP-1, Strongylocentrotus VAMP, Drosophila sybA, synB, synC, synD, or syn, Hirudo VAMP, Xenopus VAMP-2 or VAMP-3, Canio VAMP-1 or VAMP-2, Loligo VAMP, Lymnaea VAMP, Aplysia VAMP, or Caenorhabditis SNB1-like.

The cleavage site of neurotoxin may be derived from a protein that is recognized and cleaved by BoNT/C protease, or a mutant thereof. The protein may be Syntaxin or ortholog, paralog, or homolog thereof. The protein may be for example, Human or mouse Syntaxin 1A, Syntaxin 1B1, Syntaxin 2-1, Syntaxin 2-2, Syntaxin 2-3, Syntaxin 3A or Syntaxin 1B2, bovine or rat Syntaxin 1A, Syntaxin 1B1 or Syntaxin 1B2, rat Syntaxin 2 or Rat syntaxin 3, mouse Syntaxin 1A, Syntaxin 1B1, Syntaxin 1B2, Syntaxin 2, Syntaxin 3A, Syntaxin 3B or Syntaxin 3C, chicken Syntaxin 1A or Syntaxin 2; Xenopus Syntaxin 1A or Syntaxin 1B, Danio Syntaxin 1A, Syntaxin 1B or Syntaxin 3, Torpedo Syntaxin 1A or Syntaxin 1B, Strongylocentrotus Syntaxin 1A or Syntaxin 1B, Drosophila Syntaxin 1A or Syntaxin 1B, Hirudo Syntaxin 1A or Syntaxin 1B, Loligo Syntaxin 1A or Syntaxin 1B, Lymnaea Syntaxin 1A or Syntaxin 1B, or an ortholog, paralog, or homolog thereof.

The recombinant polynucleotide may contain a regulatory sequence that allows the first polynucleotide to be expressed in a cell. The recombinant polynucleotide may be an expressible recombinant polynucleotide. The regulatory sequence may be a promoter, an enhancer, a terminator sequence, or a combination thereof. The cell may be able to be bound to and internalized in the protease.

Regarding the recombinant polynucleotide, the protease may be a neurotoxin polypeptide, and the cell may undergo binding to the neurotoxin polypeptide, internalization of the neurotoxin, releasing the neurotoxin inside the cell, or a combination of the binding, the internalization, and the releasing. The cells may be cells capable of being intoxicated by the neurotoxin of the *Clostridium* genus. The neurotoxin polypeptide may be a *botulinum* toxin serotype A (BoNT/A), BoNT/B, BoNT/C, BoNT/D, BoNT/CD, BoNT/DC, BoNT/E, BoNT/F, BoNT/FA, BoNT/G, tetanus neurotoxin (TeNT), or a mutant thereof. The cell may be an endocrine cell or the like. The cell may be a primary neuron, a neuroblastoma cell, or a neuron differentiated from a pluripotent stem cell.

The recombinant polynucleotide may be a vector. The vector may be an expression vector. The vector may be a viral vector, a plasmid vector, or a linear nucleic acid construct.

The recombinant polynucleotide may further include a bicistronic sequence linked to upstream or downstream of the first polynucleotide. The bicistronic sequence may be a nucleotide sequence that enables 5'-cap independent translation. The bicistronic sequence may be a nucleotide sequence that allows a ribosome to synthesize two or more polypeptides from an mRNA with one 5'-cap during translation to synthesize a polypeptide from mRNA. The bicistronic sequence may be an internal ribosomal entry site (IRES) sequence or a nucleotide sequence that allows ribosome to skip forming of a peptide bond. The bicistronic sequence that allows the ribosome to skip forming peptide bonds may be a polynucleotide sequence (for example, SEQ ID NOS: 5, 19, 21, or 23) encoding P2A, T2A, E2A, or F2A (for example, SEQ ID NOS: 13, 20, 22, or 24).

The recombinant polynucleotide may further include a polynucleotide encoding an internal standard reporter operably linked upstream or downstream of the bicistronic sequence. The internal standard reporter may be different from the reporter moiety. The internal standard reporter may be a material that emits a detectable signal or a material that is converted into a material emitting a detectable signal in a reaction catalyzed thereby. The internal standard reporter may be selected from a fluorescence protein, β-lactamase, β-galactosidase, alkaline phosphatase, chloramphenicol acetyltransferase, β-glucouronidase, peroxidase, and luciferase. The fluorescence protein may be selected from GFP, YFP, Citrine, CFP, RFP, Kaede, PA-GFP, Emerald, Venus, DsRed, mHoneydew, mBanana, mOrange, tdTomato, mTangerine, mStrawberry, mCherry, mRasberry, mPlum, ZsGreen, and ZsYellow protein.

FIG. 1 shows a view illustrating the structure of a recombinant polynucleotide according to an aspect. Referring to A and B of FIG. 1, R represents a nucleotide sequence encoding a reporter moiety, S represents a nucleotide sequence encoding a substrate moiety, and D represents a nucleotide sequence encoding a destabilization moiety. Referring to B of FIG. 1, I represents a nucleotide sequence encoding an internal standard reporter, and B represents a nucleotide sequence encoding a bicistronic sequence. In FIG. 1, the recombinant polynucleotide is described from left to right in the order of 5'→3'. As shown in A of FIG. 1, the recombinant polynucleotide may have the structure of R-S-D. However, this structure is an example only. In one or more embodiments, the recombinant polynucleotide may further include an additional -S- between R and D to encode at least two, for example, at least three or four substrate moieties. In one or more embodiments, the recombinant polynucleotide may further include two or more -D structures, for example, at least three or four destabilization moieties. As shown in A of FIG. 1, the recombinant polynucleotide has the structure of I-B-R-S-D. However, this structure is an example only. In one or more embodiments, the recombinant polynucleotide may further include an additional -I-B- structure linked to 5' position to encode at least two, for example, at least three or four internal standard reporters. The recombinant polynucleotide may have the structure of R-S-D-B-I. However, this structure is an example only. In one or more embodiments, the recombinant polynucleotide may further include an additional -B-I- structure linked to 3' position to contain a nucleotide sequence that encodes at least two, for example, at least three or four internal standard reporters.

FIG. 2 shows the structure of a recombinant polynucleotide according to an aspect and a reaction between a polypeptide expressed thereby and a protease. Referring to FIG. 2, the polypeptide expressed by the recombinant polynucleotide according to an aspect is cleaved at the cleavage site of a substrate moiety in the presence of a protease and fragmented into a reporter moiety fragment and the remainder.

FIG. 3 shows a case where a recombinant polynucleotide according to an aspect contacts a protease in a cell. Referring to FIG. 3, the polypeptide expressed by the recombinant polynucleotide according to an aspect is cleaved at the cleavage site of a substrate moiety in the presence of a protease and fragmented into a reporter moiety fragment and the remainder.

As illustrated in FIG. 3, when a protease is transfected in a cell (top), a polypeptide having the R-S-D structure is cleaved at the S site, and thus, the reporter moiety is separated from the destabilization moiety (D) and stabilized compared to when the destabilization moiety (D) is transfected. Accordingly, signals emitted from the reporter moiety or a material derived therefrom are stronger than when the destabilization moiety (D) is transfected. The bottom part of FIG. 3 shows that when a protease is not present in the cell, the polypeptide having the R-S-D structure retains the destabilization moiety (D), and thus, the level of the polypeptide having the R-S-D structure is lowered by the destabilization moiety (D) and accordingly, a signal measured therefrom is also reduced.

FIG. 4 shows a view showing a case where a recombinant polynucleotide having a nucleotide sequence encoding an internal standard reporter according to an aspect is in contact with a protease in a cell. Referring to FIG. 4, the polypeptide expressed by the recombinant polynucleotide according to an aspect is cleaved at the cleavage site of a substrate moiety in the presence of a protease and fragmented into a reporter moiety fragment and the remainder.

As illustrated in FIG. 4, when a protease is transfected in a cell (A), a polypeptide having the R-S-D structure is cleaved at the S site, and thus, the reporter moiety is separated from the destabilization moiety (D) and stabilized compared to when the destabilization moiety (D) is transfected. Accordingly, signals emitted from the reporter moiety or a material derived therefrom are stronger than when the destabilization moiety (D) is transfected. The bottom part (B) of FIG. 4 shows that when a protease is not present in the cell, the polypeptide having the R-S-D structure retains the destabilization moiety (D), and thus, the level of the polypeptide having the R-S-D structure is lowered by the destabilization moiety (D) and accordingly, a signal measured therefrom is also reduced. In FIG. 4, the internal standard reporter protein expressed from the recombinant polynucleotide is expressed in cells regardless of the presence or absence of protease. On the other hand, the R-S-D polypeptide is synthesized by 5'-cap-independent translation by the bicistronic sequence. Thus, signals emitted from the internal standard reporter may be used to standardize the conditions for expression of the recombinant polynucleotide in a host cell.

A second aspect provides a host cell containing the recombinant polynucleotide. The host cell may be able to translocate the protease into the cell, for example, into the cytoplasm. The host cell may be a cell that may translocate a protease, for example, a neurotoxin polypeptide into a cell, for example, into the cytoplasm. The host cell may bind to, for example, a protease via a receptor and translocate a complex formed thereby into a cell, for example, into the cytoplasm. However, embodiments of the present disclosure should not be construed as limited to any particular translocation mechanism. The host cell may be a cell capable of expressing a polynucleotide encoding a protease, for example, a proteolytic activity neurotoxin polypeptide in the cytoplasm. The host cell may include a polynucleotide encoding a protease, for example, a proteolytic activity neurotoxin polypeptide in the cytoplasm. The polynucleotide encoding a protease, for example, a proteolytic activity neurotoxin polypeptide may be inserted into a chromosome, or extrachromosomal-transfected. The polynucleotide encoding a protease, for example, a proteolytic activity neurotoxin polypeptide may be transiently or permanently expressed. The polynucleotide encoding a protease, for example, a proteolytic activity neurotoxin polypeptide may be in its own form or in a form embedded in a vehicle such as a vector. The polynucleotide may be introduced from outside the host cell. The host cell may be a recombinant cell. The host cell may be an endocrine cell. The cell may be selected from a primary neuron, a neuroblastoma cell, and a neuron differentiated from a pluripotent stem cell.

The host cell may be able to express the recombinant polynucleotide. The host cell may express, from the recombinant polynucleotide, a polypeptide including a reporter moiety, a destabilization moiety, and a substrate moiety operatively linking the destabilization moiety to the reporter moiety, wherein the substrate moiety has a cleavage site of protease activities, or the polypeptide and the internal standard reporter protein.

A third aspect provides a kit for determining proteolytic activities of a protease, for example, a neurotoxin polypeptide, the kit including a polypeptide encoded by the recombinant polynucleotide described above and a detection agent that measures signals emitted by a reporter moiety, an internal standard reporter, or a product thereof. Regarding the kit, the reporter may be luciferase, the kit may further include a luciferase substrate, and the detection agent may be used to measure the enzymatic conversion of the luciferase substrate. For example, the detection agent may be a photodetector. The reporter may be a fluorescence protein, and the detection agent may be used to measure fluorescence emitted by the fluorescence protein. For example, the detection agent may be a device that excites the fluorescence protein with excitation light and measures the emitted fluorescence. The internal standard reporter may be different from the reporter moiety. The internal standard reporter may be a luciferase or a fluorescence protein, each being different from the reporter moiety.

A fourth aspect provides a kit for determining proteolytic activities of a protease, for example, a neurotoxin polypeptide, the kit including a host cell including the recombinant polynucleotide described above and a detection agent that measures signals emitted by a reporter moiety, an internal standard reporter, or a product thereof. Regarding the kit, the reporter may be luciferase, the kit may further include a luciferase substrate, and the detection agent may be used to measure the enzymatic conversion of the luciferase substrate. The reporter may be a fluorescence protein, and the detection agent may be used to measure fluorescence emitted by the fluorescence protein. For example, the detection agent may be a device that excites the fluorescence protein with excitation light and measures the emitted fluorescence. The internal standard reporter may be different from the reporter moiety. The internal standard reporter may be a luciferase or a fluorescence protein, each being different from the reporter moiety.

A fifth aspect provides a method of determining protease activities in a sample, the method including: contacting a polypeptide encoded by the recombinant polynucleotide with a sample suspected of containing a protease polypeptide; and measuring signals emitted by the reporter moiety or a product thereof in a product obtained by the contacting.

A sixth aspect provides a method of determining characteristics of a protease polypeptide in a sample, the method including contacting a polypeptide encoded by the recombinant polynucleotide with a protease polypeptide; measuring signals emitted by the reporter moiety or product thereof in a product obtained by the contacting; and determining, based on measured signals, one or more selected from an onset time of signal emission and a time duration of signal emission.

The methods according to the 5th and 6th aspects each include contacting the polypeptide encoded by the recombinant polynucleotide with a sample suspected of containing a protease polypeptide or a protease. The contacting may be carried out under conditions that allow the cleavage site of protease activities in the polypeptide to degrade. The protease may be a neurotoxin polypeptide.

The contacting may be performed in a liquid medium. The liquid medium may be conditioned to allow the proteolytic activity of the protease to work. The conditions may include a pH, temperature, a cofactor, a salt concentration, and a combination of these. The liquid medium may be a buffer solution such as a phosphate buffered saline (PBS).

The methods according to the 5th and 6th aspects include measuring signals emitted by the reporter moiety or a product thereof in a product obtained by the contacting. When the reporter moiety is a polypeptide that emits a detectable signal, signals may be directly measured. For example, when the reporter moiety is a fluorescence protein such as GFP, the fluorescence may be measured. The measuring of the fluorescence may be by irradiating the product obtained by the contacting with excitation light and measuring light emitted from the product obtained by the contacting. The wavelength of the excitation light and emission light may be appropriately selected according to the selected fluorescence protein. When the reporter moiety is a polypeptide that converts to a material that emits a detectable signal in a reaction catalyzed by the reporter moiety, the method may further include adding a substrate required for the catalytic activity of the reporter moiety to the product obtained by the contacting to convert the material into a material that emits a detectable signal. Next, a signal emitted by a material emitting a detectable signal is measured. For example, the reporter moiety is luciferase, and the contacting and the measuring of a signal may be performed to add a luciferase substrate in the reaction solution, and the detecting is performed to measure the enzymatic conversion of the luciferase substrate. The luciferase substrate may be luciferin.

The methods according to the 5th and 6th aspects may each further include comparing the measured signal with a signal emitted by a control group. The control group may be measured in the same procedure, except that a sample used does not include protease, for example, neurotoxin polypeptide or does include a known concentration of protease for example, neurotoxin polypeptide. Each of the methods may further include determining the level of protease in a sample based on the correlation between a signal obtained by the comparing and the level of protease in the sample.

The method according to a 6th aspect includes determining at least one of an onset time of signal emission and a time duration of signal emission based on the measured signal. The at least one of an onset time of signal emission and a duration of the emission of the signal may be easily determined by one of ordinary skill in the art based on the measured signals. For example, one of ordinary skill in the art may determine an onset time of emission and a time duration, based on signal values representing protease activities over time, for example, emitted signals. The signal values representing protease activities over time may determine an onset time of emission and a time duration, based on measured values of signals emitted over time. The at least one of an onset time of signal emission and a duration of the emission of the signal may depend on types of protease. When the reporter moiety is a polypeptide that emits a detectable signal, degradation of the cleavage site by protease activities may lead to an increase in the emitted signal and a decrease in the emitted signal when protease activities disappear. For example, when measured under the same conditions, at least one of the onset time of the signal and the time duration of the signal may be changed depending on characteristics of the protease. In one embodiment, the protease may be distinguished from other proteases in terms of, in addition to this relative comparison, the absolute value of at least one of the onset time of the signal emission, and time duration of the signal, or a range thereof. Thus, the determining may include comparing at least one of the onset time of signal emission and the time duration of the signal of a known protease, or determining characteristics of a protease based on an absolute value of at least one of the onset time of signal emission and the time duration of the signal or a range thereof. According to the at least one of the onset time of signal emission and the time duration of the signal, indication to be treated by the protease may vary. Thus, each of the methods may include determining an indication to be treated in a subject by the protease, based on the determined characteristics of the protease.

A seventh aspect provides a method of determining protease activities in a sample, the method including: contacting the host cell with a sample suspected of containing a protease polypeptide; and measuring signals emitted by the reporter moiety, the internal standard reporter, or a product thereof in a product obtained by the contacting.

An eighth aspect provides a method of determining characteristics of protease polypeptide in a sample, the method including contacting the host cell with the protease polypeptide; measuring signals emitted by the reporter moiety, the internal standard reporter, or product thereof in a product obtained by the contacting; and determining, based on measured signals, one or more selected from an onset time of emission of the signals and a duration thereof.

Each of the methods according to the 7th and 8th aspects includes contacting the host cell with a sample suspected of containing a protease polypeptide. The contacting may be carried out under conditions that allow the cleavage site of protease activities to degrade. The protease may be a neurotoxin polypeptide. The contacting may be performed in a liquid medium. The liquid medium may be conditioned to allow the proteolytic activity of the protease to work. The conditions may include a pH, temperature, a cofactor, a salt concentration, and a combination of these. The liquid medium may be a buffer solution such as a phosphate buffered saline (PBS), or a medium in which the host cell is cultured.

Regarding the methods according to the 7th and 8th aspects, the host cell may be able to translocate the protease into the cell, for example, into the cytoplasm. The host cell may be a cell that may translocate a protease, for example, a neurotoxin polypeptide into a cell, for example, into the cytoplasm. The host cell may bind to, for example, a protease via a receptor and translocate a complex formed thereby into a cell, for example, into the cytoplasm. However, embodiments of the present disclosure should not be construed as limited to any particular translocation mechanism. The host cell may be a cell capable of expressing a polynucleotide encoding a protease, for example, a proteolytic activity neurotoxin polypeptide in the cytoplasm. The host cell may include a polynucleotide encoding a protease, for example, a proteolytic activity neurotoxin polypeptide in the cytoplasm. The polynucleotide encoding a protease, for example, a neurotoxin polypeptide having a proteolytic activity may be inserted into a chromosome, or may be present outside a chromosome. The polynucleotide encoding a protease, for example, a neurotoxin polypeptide having a proteolytic activity may be transiently or stably expressed. The polynucleotide encoding a protease, for example, a proteolytic activity neurotoxin polypeptide may be in its own form or in a form embedded in a vehicle such as a vector. The polynucleotide may be introduced from outside the host cell. The host cell may be a recombinant cell. The host cell may be an endocrine cell. The host cell may be selected from a primary neuron, a neuroblastoma cell, and a neuron differentiated from a pluripotent stem cell. The host cell may be able to express the recombinant polynucleotide. The host cell may express, from the recombinant polynucleotide, a polyp eptide including a reporter moiety, a destabilization moiety, and a substrate moiety operatively linking the destabilization moiety to the reporter moiety, wherein the substrate moiety has a cleavage site of protease activities, or the polypeptide and the internal standard reporter protein.

The methods according to the 7th and 8th aspects include measuring signals emitted by the reporter moiety or the internal standard reporter or a product thereof in a product obtained by the contacting. When the reporter moiety or the internal standard reporter is a polypeptide that emits a detectable signal, signals may be directly measured. For example, when the reporter moiety is a fluorescence protein such as GFP, the fluorescence may be measured. The measuring of the fluorescence may be by irradiating the product obtained by the contacting with excitation light and measuring light emitted from the product obtained by the contacting. The wavelength of the excitation light and emission light may be appropriately selected according to the selected fluorescence protein. When the reporter moiety or the internal standard reporter is a polypeptide that converts to a material that emits a detectable signal in a reaction catalyzed by the reporter moiety, the method may further include adding a substrate required for the catalytic activity of the reporter moiety to the product obtained by the contacting to convert the material into a material that emits a detectable signal. Next, a signal emitted by a material emitting a detectable signal is measured. For example, the reporter moiety or the internal standard reporter is luciferase, and the contacting and the measuring of a signal may be performed to add a luciferase substrate in the reaction solution, and the detecting is performed to measure the enzymatic conversion of the luciferase substrate. The luciferase substrate may be luciferin. For example, the reporter moiety is luciferase, and the contacting and the measuring of a signal may be performed to add a luciferase substrate in the reaction solution, and the detecting is performed to measure the enzymatic conversion of the luciferase substrate. The luciferase substrate may be luciferin.

In the methods according to the 7th and 8th aspects, the reporter may be a fluorescence protein, and the measuring may be performed to measure fluorescence emitted by the fluorescence protein.

The methods according to the 7th and 8th aspects may each further include comparing the measured signal with a signal measured from a control group. The control group may be measured in the same procedure, except that a sample used does not include neurotoxin polypeptide or does include a known concentration of neurotoxin polypeptide. Each of the methods may further include determining the level of neurotoxin polypeptide in a sample based on the correlation between a signal obtained by the comparing and the level of neurotoxin in the sample.

According to each of the methods according to the 7th and 8th aspects, the recombinant polynucleotide further includes a polynucleotide encoding a bicistronic sequence linked upstream or downstream of a first polynucleotide and an internal standard reporter operably linked upstream or downstream of the bicistronic sequence. In this case, each of the methods may further include measuring a signal emitted by the internal standard reporter. Each of the methods may further include determining the level of a signal emitted by the reporter moiety relative to the signal emitted by the internal standard reporter.

The method according to the 8th aspect includes determining at least one of an onset time of signal emission and a time duration of signal emission based on measured signals. The at least one of an onset time of signal emission and a time duration of signal emission may be easily determined by one of ordinary skill in the art based on the measured signals. For example, one of ordinary skill in the art may determine signal values representing protease activities over time, for example, an onset time of signal emission and a time duration of signal emission, measured based on emitted signals. The signal values representing protease activities over time, that is, an onset time of signal emission and a time duration of signal emission may be determined based on measurements of emitted signals over time. The at least one of an onset time of signal emission and a time duration of signal emission may depend on types of protease. When the reporter moiety is a polypeptide that emits a detectable signal, degradation of the cleavage site by protease activities may lead to an increase in the emitted signal and a decrease in the emitted signal when protease activities disappear. For example, when measured under the same conditions, one or more of an onset time of signal emission and a time duration of signal emission may be changed depending on characteristics of the protease. In one embodiment, the protease may be distinguished from other proteases in terms of, in addition to this relative comparison, the absolute value of at least one of the onset time of the signal emission, and time duration of the signal, or a range thereof. Thus, the determining may include comparing at least one of the onset time of signal emission and the time duration of the signal of a known protease, or determining characteristics of a protease based on an absolute value of at least one of the onset time of signal emission and the time duration of the signal or a range thereof. According to the at least one of the onset time of signal emission and the time duration of the signal, indication to be treated by the protease may vary. Thus, each of the methods may include determining an indication to be treated in a subject by the protease, based on the determined characteristics of the protease.

The method according to the 8th aspect may include determining at least one of an onset time of signal emission and a time duration of signal emission based on measured signals, without cellular damage, for example, cell lysis.

A 9th aspect provides a method of measuring an ability of a host cell in expressing or inhibiting a protease, the method including: introducing a polynucleotide encoding a protease polypeptide into the host cell; and culturing the host cell to which the polynucleotide has been introduced and measuring signals emitted by the reporter moiety or the internal standard reporter or the product thereof in a culture.

The method includes introducing a polynucleotide encoding a protease polypeptide into the host cell. The host cell and the protease are the same as described above. The introducing may be performed by, for example, transformation, transfection, or transduction. The host cell may be a cell capable of expressing a polynucleotide encoding a protease, for example, a neurotoxin polypeptide having a proteolytic activity in the cytoplasm. The host cell may include a polynucleotide encoding a protease, for example, a neurotoxin polypeptide having proteolytic activity. The polynucleotide encoding a protease, for example, a neurotoxin polypeptide having a proteolytic activity may be inserted into a chromosome, or may be present outside a chromosome. The polynucleotide encoding a protease, for example, a neurotoxin polypeptide having a proteolytic activity may be transiently or stably expressed. The polynucleotide encoding a protease, for example, a proteolytic activity neurotoxin polypeptide may be in its own form or in a form embedded in a vehicle such as a vector. The polynucleotide may be introduced from outside the host cell. The host cell may be a recombinant cell. The host cell may be an endocrine cell. The host cell may be selected from a primary neuron, a neuroblastoma cell, and a neuron differentiated from a pluripotent stem cell.

The method includes culturing the host cell to which the polynucleotide has been introduced and measuring signals emitted by the reporter moiety or the internal standard reporter or the product thereof in a culture. The culturing may be performed in the presence of a test material. The test material may be a polymer, such as a protein, and a polysaccharide, or a small molecule compound. The test material may be a material that is considered to inhibit or promote the protease. The host cell may be one to which a polynucleotide encoding the candidate test material has been introduced. Thus, the method may be a method of screening for a material that modulates protease activities. The screening method may include comparing a test group signal obtained by using a test material and a control signal obtained by using a control group. The control group may be a positive control group using a material that is known to control protease activities or a negative control group obtained in the same manner as used to the test group except for the candidate test material. The method may include determining whether the candidate test material is a material that modulates protease activities based on comparison results obtained from the comparing operation. In one embodiment, when the test group signal is greater than the signal of the negative control group, it may be determined that the material has an activity of promoting protease activities. In one embodiment, when the test group signal is smaller than the signal of the negative control group, it may be determined that the material has an activity of inhibiting protease activities.

DESCRIPTION OF THE DRAWINGS

FIG. 5 shows measurements of activities of a reporter moiety after NG108-15 cells transfected with pFB vector 1 were differentiated into neurons and then intoxicated with *botulinum* toxin A.

FIG. 10 shows measurements of activities of a reporter moiety and an internal standard reporter protein each expressed by NG108-15 cells transfected with pFB vector 6 after the cells were differentiated into neurons and then transient-transfected with pCDNA4_BLC vector expressing a light chain of *botulinum* toxin B.

FIG. 11 shows measurements of signals emitted by a reporter moiety protein expressed by NT2 cells transfected with pFB vector 2 after the cells are established as a stabilized monoclonal-derived cell line, differentiated into neurons, and then, intoxicated with different concentrations of BoNT/A.

FIGS. 12 to 14 show measurements of signals emitted by a reporter moiety protein or an internal standard reporter each expressed by NT2 cells transfected with pFB vector 2 after the cells are established as a stabilized monoclonal-derived cell line, differentiated into neurons, and then, intoxicated with different concentrations of BoNT/A.

MODE OF THE INVENTION

Figure 1:
FIG. 1 shows a view illustrating the structure of a recombinant polynucleotide according to an aspect.
Figure 1:
Figure 2:
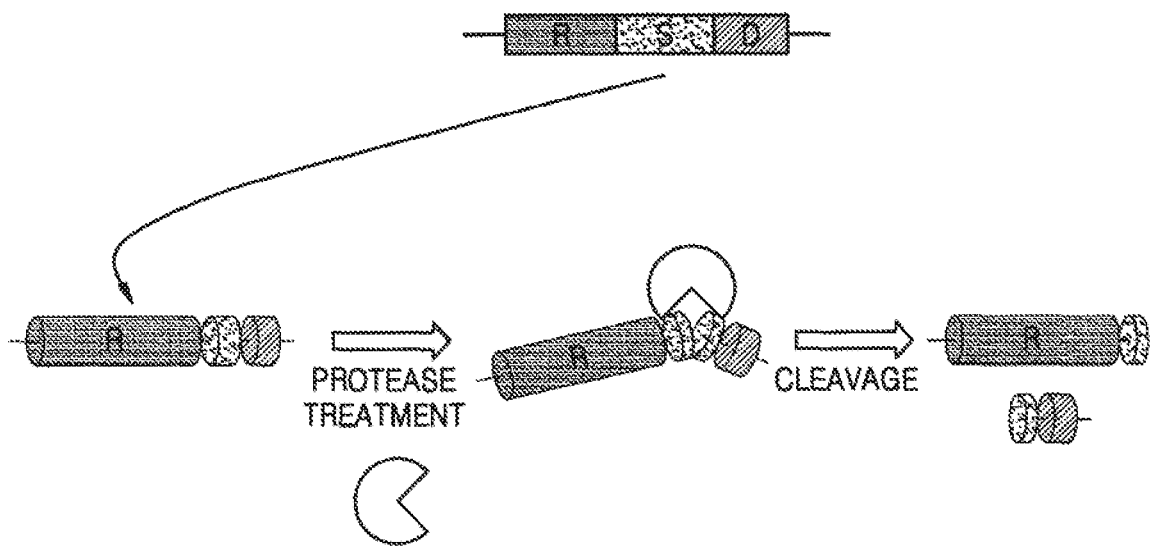
FIG. 2 shows the structure of a recombinant polynucleotide according to an aspect and a reaction between a polypeptide expressed thereby and a protease.
Figure 3:
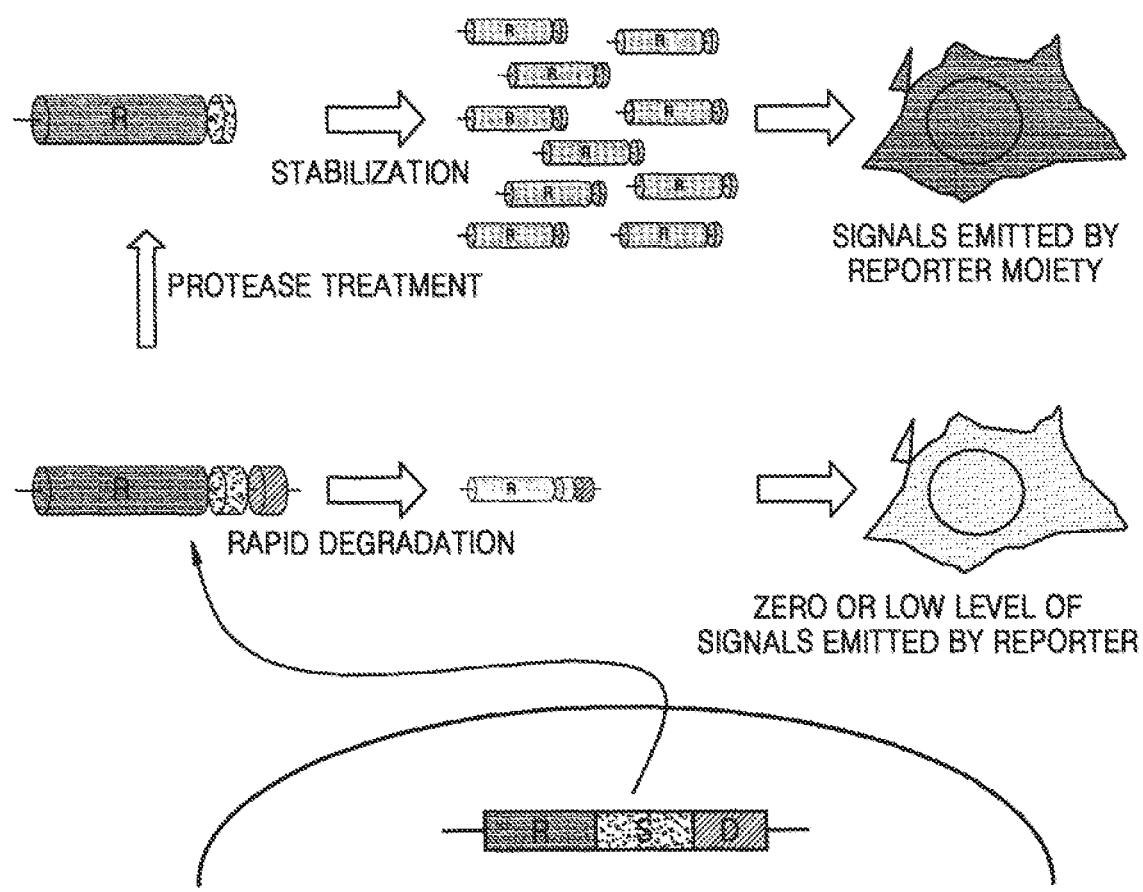
FIG. 3 shows a case where a recombinant polynucleotide according to an aspect contacts a protease in a cell.
Figure 4:
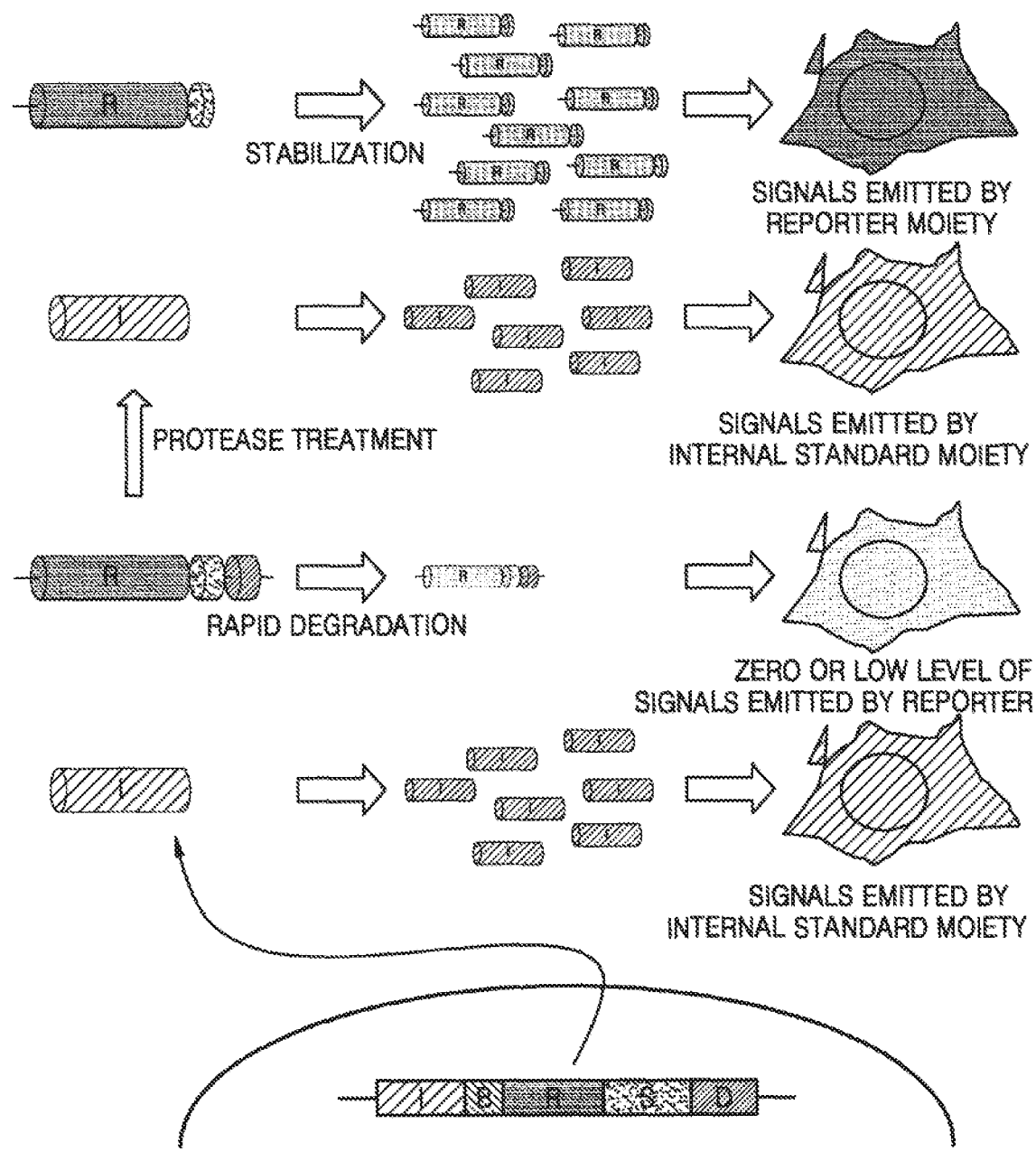
FIG. 4 shows a view showing a case where a recombinant polynucleotide having a nucleotide sequence encoding an internal standard reporter according to an aspect is in contact with a protease in a cell.

Hereinafter, the present invention will be described in more detail with reference to examples. However, these examples are for illustrative purposes only, and the scope of the present invention is not limited to these examples.

Example 1

Preparation of recombinant polynucleotide encoding a reporter moiety-substrate moiety-destabilization moiety (hereinafter also referred to as 'R-S-D') polypeptide and cells containing the recombinant polynucleotide (1) Preparation of Recombinant Polynucleotide Encoding a Reporter Moiety-Substrate Moiety-Destabilization Moiety (Hereinafter Also Referred to As 'R-S-D') Polypeptide Two recombinant polynucleotide having different structures were prepared. One is to encode a polypeptide having an R-S-D structure and the other is to encode a polypeptide having an I-B-R-S-D structure. Here, I indicates a nucleotide sequence encoding an internal standard reporter, and B indicates a bicistronic sequence. The recombinant polynucleotide is in the form of a plasmid vector.

A nucleotide sequence encoding a luminescence or fluorescence protein was used as the internal standard reporter or the reporter moiety. Examples of the sequence encoding the luminescence protein are a nucleotide sequence (for example, SEQ ID NO: 1) encoding a firefly luciferase (FLuc) protein (for example, SEQ ID NO: 9) and a nucleotide sequence (for example, SEQ ID NO: 2) encoding a nano-luciferase (NLuc) protein (SEQ ID NO: 10), and examples of the sequence encoding the fluorescence protein are a nucleotide sequence (SEQ ID NO: 3) encoding an enhanced green fluorescence protein (eGFP) (SEQ ID NO: 11) or a nucleotide sequence (SEQ ID NO: 4) encoding an mCherry protein (SEQ ID NO: 12).

The bicistronic sequence used herein is a nucleotide sequence (P2A) (SEQ ID NO: 5) encoding a self-cleaving peptide derived from porcine teschovirus-1.

The substrate moiety of a proteolytic enzyme used herein is, in the case of *botulinum* toxin type A, a nucleotide sequence (SEQ ID NO: 6) encoding an amino acid sequence (SEQ ID NO: 14) from 145 to 207 of the total of 207 amino acid sequence as a C-terminal region of human SNAP25, or, in the case of *botulinum* toxin type B, a nucleotide sequence (SEQ ID NO: 17) encoding human VAMP2 (SEQ ID NO: 18).

The destabilization moiety used herein is a nucleotide sequence (SEQ ID NO: 8) encoding the PEST sequence (SEQ ID NO: 16) and a nucleotide sequence (SEQ ID NO: 7) encoding CL1 sequence (SEQ ID NO: 15).

The recombinant polynucleotide was constructed as follows:

First, a nucleotide sequence (SEQ ID NO: 1) (hereinafter referred to as 'FLuc sequence') encoding firefly luciferase (FLuc)(SEQ ID NO: 9) was obtained from pGL4.31 vector (Promega), a nucleotide sequence (SEQ ID NO: 2) (hereinafter referred to as 'NLuc sequence') encoding nano-luciferase (NLuc) (SEQ ID NO: 10) was obtained from pNL1.1 vector (Promega), a nucleotide sequence(SEQ ID NO: 3)(hereinafter referred to as 'eGFP sequence') encoding enhanced green fluorescent protein (eGFP) (SEQ ID NO: 11) was obtained from pEGFP-C1 vector (clontech), and a nucleotide sequence (SEQ ID NO: 4)(hereinafter referred to as 'mCherry sequence') encoding mCherry (SEQ ID NO: 12) was obtained from pmCherry-C1 vector. A nucleotide sequence (SEQ ID NO: 6) encoding an amino acid sequence from 145 to 207 of the total of 207 amino acid sequence as a C-terminal region of human SNAP25 (hereinafter referred to as 'SNAP25 sequence'), and a nucleotide sequence encoding human VAMP2 (hereinafter referred to as 'VAMP2 sequence') were synthesized by RT-PCR from mRNA of human-derived cell lines. A sequence encoding CL1-PEST polypeptide in which CL1 is fused with PEST (hereinafter referred to as 'CL1-PEST sequence') and a nucleotide sequence encoding a self-cleaving peptide P2A derived from porcine teschovirus-1 (hereinafter referred to as 'P2A sequence') were obtained by gene synthesis.

Next, recombinant polynucleotides having the structure of R-S-D or I-B-R-S-D were constructed by gene cloning using restriction enzyme using a combination of the sequences, and ligated to the BamHI/XhoI restriction site of the pCDNA4 vector (Invitrogen) or pFB vector (Agilent) to construct recombinant vectors. For example, a vector (hereinafter referred to as "pCDNA4 vector 1") in which a recombinant polynucleotide consisting of NLuc sequence, SNAP25 sequence, and CL1-PEST sequence is introduced to BamhI/XhoI enzyme site of pCDNA4 vector or a vector (hereinafter referred to as "pFB vector 1") in which a recombinant polynucleotide consisting of NLuc sequence, SNAP25 sequence, and CL1-PEST sequence is introduced to BamHI/XhoI enzyme site of pFB vector were constructed. For example, a vector (hereinafter referred to as "pCDNA4 vector 2") in which a recombinant polynucleotide consisting of mCherry sequence, SNAP25 sequence, and CL1-PEST sequence is introduced to BamH/IXhoI enzyme site of pCDNA4 vector or a vector (hereinafter referred to as "pFB vector 2") in which a recombinant polynucleotide consisting of mCherry sequence, SNAP25 sequence, and CL1-PEST sequence is introduced to BamHI/XhoI enzyme site of pFB vector were constructed. For example, a vector (hereinafter referred to as "pCDNA4 vector 3") in which a recombinant polynucleotide consisting of FLuc sequence, P2a sequence, NLuc sequence, SNAP25 sequence, and CL1-PEST sequence is introduced to BamHI/XhoI enzyme site of pCDNA4 vector or a vector (hereinafter referred to as "pFB vector 3") in which a recombinant polynucleotide consisting of FLuc sequence, P2a sequence, NLuc sequence, SNAP25 sequence, and CL1-PEST sequence is introduced to BamHI/XhoI enzyme site of pFB vector were constructed. A pFB vector (hereinafter referred to as "pFB vector 4") in which a recombinant polynucleotide consisting of FLuc sequence, P2a sequence, NLuc sequence, VAMP2 sequence, and CL1-PEST sequence is introduced to BamH/XhoI enzyme site of pFB vector, was constructed.

Here, the pCDNA4 vector is a plasmid-derived vector and used to transiently express the recombinant polynucleotides in cells. The pFB vector used herein was a vector derived from moloney murine leukemia virus (MMLV), and used to construct a cell line modified by transfection, that is, a cell line in which the recombinant polynucleotides were introduced into a chromosome.

The structures of the constructed plasmid vectors and the viral vectors were confirmed by sequencing, and the plasmid vector DNA was purified and isolated to the level for cell culture.

(2) Production of Cells Expressing R-S-D or I-B-R-S-D Polypeptide

In order to construct a cell line that stably and constantly expressing the vectors constructed in (1), transduction with MMLV-derived viral vector, that is, pFB vector, was performed. The transfection with MMLV-derived viral vector is a widely practiced method in the art, and the reference (Felts Ka et al., Mol Biotechnol. 2002 Sep. 22(1):25-32.). Briefly, HEK-293T cells (ATCC-CRL-3216), a cell for packaging, were seeded in 10 ml of DMEM medium containing 10% fetal bovine serum (FBS) at the population of $1\times10^7$ cells in a 55 $cm^2$ culture dish, and cultured for 24 hours in a 37° C. and 5% $CO_2$ incubator, and then, the recombinant polynucleotide pFB vector according to the present invention, that is, pFB vector 1, 2, 3, or 4, and pCMV-gagpol (Cell Biolabs, inc.) and pCMV-VSV-G (Cell Biolabs, inc.) were mixed at a ratio of 3:2:1. At this time, pFB vector was used in an amount of 7.5 μg. The mixtures of this vector was used for transfection with Lipofectamine™ 3000 (Invitrogen) and the transduction method was performed according to the manufacturer's instructions. Cells were cultured under the same conditions for 48 hours after transduction. Thus, an infectious packaged pFB vector 1,2,3 or 4-containing virus was produced from the HEK 293T cells.

Then, the infectious packaged pFB vector 1,2,3 or 4-containing virus was transfected into a target cell to produce a cell line that enables stable, constant expression. The target cell used herein was NG108-15 cell(ATCC-HB-12317), SiMa cell(DSMZ: ACC-164), and NT2 cell(ATCC-CRL-1973). NG108-15 cells are hybrid cells of neuroblastoma of rat and glioma of rat, and a cell line that has been identified as susceptible to *botulinum* toxin type A through differentiation into neurons (Whitemarsh R C et al., Biochem Biophys Res Commun. 2012 Oct. 19; 427(2): 426-30). SiMa cells are a cell line that is derived from human neuroblastoma and have been identified as susceptible to *botulinum* toxin type A through differentiation into neurons (Fernandez-Salas E et al., PLoS One. 2012; 7(11): e49516). NT2 cells are an embryonal carcinoma cell line derived from human testicles, have multiple differentiation potential, and may undergo differentiation into neurons under specific conditions, and when differentiated into neurons, the NT2 cells were found to be susceptible to *botulinum* toxin type A (Tegenge et al., Cell Mol Neurobiol. 2012 August; 32(6): 1021-9).

The specific procedure of a cell line that expresses a target polypeptide stably is as follows.

First, a target cell was seeded in a 24-well plate containing 0.5 ml of DMEM medium containing 10% FBS at the population of about $1 \times 10^5$ cells per well one day before infection, and then, cultured in a 5% $CO_2$ incubator at a temperature of 37° C. for one day. The culture supernatant of HEK-293T cells collected therefrom was filtered using a 0.45-μm syringe filter to obtain a viral solution in which cells and cell debris were removed. The viral solution was added to wells in which the target cell had been cultured and from which the culture medium had been removed, with a concentration of 1 ml/well (24-well), and the cells were cultured under the same conditions for 6 hours to induce infection. Polybrene was added at a level of 8 mg/ml to increase the efficiency of infection into a target cell. After 6 hours, the medium was replaced with DMEM medium containing 10% FBS as a medium for normal cell culture, and the cells were cultured under the same conditions for 2 days.

Next, the infected target cell in the 24-well was cultured for 2 days, and then, transferred to a 55 $cm^2$ culture dish, and cultured after 500 to 1000 μg/ml of geneticin (Gibco), a selective antibiotic of the pFB vector, was added thereto. The appropriate dose of antibiotic was determined based on the titration of the target cell and geneticin. When NT2 cells were the target cell, they were cultured in a culture dish containing 10 ml of cell culture medium in the presence of 800 μg/ml of geneticin for 5 days.

Next, to form a single cell clone, the target cell was transferred to a 96-well well at the concentration of 2 cells/well. In each well of a 96-well plate containing 100 μl of the same medium used in the culturing in 55 $cm^2$ culture dish, colonies formed with single cell clones while being cultured under the same conditions for 4 weeks were selected by a cell culture microscope, and the selected colonies were subjected to expansion culture.

In this process, a pre-selection process may be performed according to the structure of a produced recombinant polynucleotide. That is, when an internal standard reporter protein is a fluorescence protein, the pre-selection process may be performed by using a fluorescence microscopy, or when an internal standard reporter protein is a luminescence protein, the pre-selection process may be performed by luminescent analysis.

To pre-select a recombinant polynucleotide in which the internal standard reporter protein is not present or to pre-select a monoclonal cell line having an excellent sensitivity from among monoclonal cell lines in which an internal standard reporter protein is present, proteasome inhibitor MG132 (Sigma) was added at a concentration of 10 μM medium, or when the recombinant polynucleotide includes SNAP25 sequence, light chain DNA of *botulinum* toxin type A was used with Lipofectamine™ 3000 (Invitrogen), and when the recombinant polynucleotide includes VAMP2 sequence, light chain DNA of *botulinum* toxin type B was used with Lipofectamine™ 3000 (Invitrogen), and the transduction was performed according to the manufacturer instructions. At this time, BoNT/A LC and BoNT B LC were introduced into the BamHI/XhoI site of pCDA4. In detail, regarding only to cells in which a monoclonal colony was identified while culturing in a 96-well for about 3 to 4 weeks, the same number of cells were seeded seperately in two 96-well plates: one plate for a screening experiment, and the other plate for maintenance culture.

Monoclone-derived cell lines obtained through these screening procedures were subjected to expansion culture, and stored frozen. The lyophilization was carried out by freezing the general mammalian cells. Briefly, $5 \times 10^1$ to $1 \times 10^7$ cells were diluted in 1 ml of a culture medium containing 5% or 10% DMSO and the diluted cells were placed in a freezing vial. The temperature was lowered to −80° C. and then stored in the gas phase of a liquefied nitrogen tank.

As a result, cell line NG108-15 cells, SiMa cells, and NT2 cells, which stably, constantly express the pFB vector 1, 2, 3, 4, or 6 containing virus, were established.

(3) Differentiation of Established NG108-15 Cells, SiMa Cells, and NT2 Cells into Neurons and Toxin Intoxication NG108-15 cells, SiMa cells, and NT2 cells are neuroblastoma cell lines or embryonal carcinoma cell line, which are known to be susceptible to *botulinum* toxin when differentiated into neurons. Therefore, these cells were differentiated into neurons according to the following procedure.

NG108-15 cells were maintenance-cultured in DMEM medium supplemented with 10 (v/v) % FBS in a 5% $CO_2$ incubator at a temperature of 37° C. For neuronal differentiation, cells were seeded at a concentration of $2 \times 10^4$ cells/well in each well of a 96-well matrigel (BD science)-coated plate for cell culture, and incubated in a neurobasal medium (Gibco) supplemented with 50 μM of retinoic acid and 25 μM of purmophamine for about 5 days. The neurobasal medium contained B27 (Gibco), Glutamax (Gibco), and non-essential amino acid (Gibco) as supplements in an amount of 1× each.

SiMa cells were maintenance-cultured in DMEM medium supplemented with 10 (v/v) % FBS in a 5% $CO_2$ incubator at a temperature of 37° C. For neuronal differentiation, cells were seeded at a concentration of $5 \times 10^4$ cells/well in each well of a 96-well matrigel (BD science)-coated plate for cell culture, and incubated in a serum-free MEM medium (Welgene) supplemented with 50 μM of retinoic acid for about 5 days. The MEM medium contained B27 (Gibco), N2

(Gibco), Glutamax (Gibco), HEPES (Gibco) and non-essential amino acid (Gibco) as supplements in amounts of 1× each.

NT2 cells (also referred to as "NTteraA2") were maintenance-cultured in α-MEM medium (Welgene) supplemented with 10 (v/v) % FBS in a 5% CO2 incubator at a temperature of 37° C. For neuronal differentiation, the cells were seeded at a concentration of 1×10$^5$ cells/ml in each well of a Petri dish and cultured in differentiation medium supplemented with 50 μM retinoic acid for 1 week under the same conditions while the medium was exchanged every 2 to 3 days. For the differentiation medium, DMEM/F12 (Welgene) medium supplemented with 10 (v/v) % FBS was used.

The cultured cells form spheres, and after 1 week of culturing, the spheres were collected and transferred to a regular cell culture plate having the same area. The cells were cultured, as adherent cells, on the differentiation medium supplemented with 50 μM of retinoic acid for 1 week while the medium was exchanged every 2 to 3 days. Subsequently, the adhered cells were deaggregated and detached by using trypsin, and the number of cells was counted.

1×10$^7$ cells were transferred to a 175T flask (Nunc) and cultured in the differentiation medium supplemented with a mitotic inhibitor for 10 days under the same conditions while the medium was exchanged every 2 to 3 days. The mitotic inhibition used herein was 1 μM AraC, 10 μM Uridine, and 10 μM Floxuridine. Cells differentiated into neurons were detached by using trypsin, and the obtained cells were stored frozen. A medium for freezing was used as the medium for the storing frozen, and the freezing was performed by cell freezing method. The differentiated neurons were seeded at the population of 1×10$^5$ cells per well in a 96-well matrigel-coated plate for cell-culture and cultured for 10 days or more in the differentiation medium, and the medium was changed every 2 to 3 days.

(4) Intoxicating of Differentiated Neurons with *Botulinum* Toxin

Intoxicating of differentiated neurons with *botulinum* toxin type A was performed as follows. For intoxicating with a purified toxin protein, the purified toxin protein was diluted to an appropriate concentration in the differentiation medium and then exchanged with the culture medium of the neuron cultured in a 5% CO$_2$ incubator at a temperature of 37° C. Thereafter, the cells were cultured under the same conditions for 24 hours to induce toxin-intoxication. Then, the medium was replaced with the differentiation medium and the cells were cultured for 72 hours under the same conditions.

The differentiation medium was added to a commercially available *botulinum* toxin drug vial (Meditoxin injectable, Neuronox) to suspend lyophilized toxin protein and excipient, and then, the differentiation medium was exchanged with the culture medium of the cells being maintainance-cultured in a 5% CO$_2$ incubator at a temperature of 37° C. The toxin potency test on final product vials was performed by using a toxin placebo vial to make the amount of excipient treated the same. The toxin placebo vial was prepared by removing only the toxin protein from the final product toxin vial.

That is, the same amount of the final product toxin vial and the toxin placebo vial were suspended in the same amount, and then, the total amount of the intoxicating medium was treated in the same manner according to each treatment concentration.

(5) Quantitative Analysis of Reporter Moiety or Internal Standard Reporter

Quantitative analysis of the reporter moiety or internal standard reporter protein expressed from the recombinant polynucleotide was performed as follows.

Regarding the recombinant polynucleotide according to the present invention, when a luminescence protein was used as a reporter moiety or an internal standard reporter protein, the luminescence protein was quantitatively analyzed by a luminescence assay. When the reporter moiety is NLuc, the Nano-luciferase assay kit (Promega) was used.

When the reporter moiety was NLuc and the internal standard reporter protein was FLuc, the One-glo dual nano-luciferase assay kit (Promega) was used and the test was performed according to the supplier's manual. The luminescence was measured by using SpectraMax (Molecular Device Inc). Normalization was performed by using a resultant value obtained by dividing the measured NLuc value by the internal standard reporter protein FLuc value.

Regarding the recombinant polynucleotide according to the present invention, when a fluorescence protein was used as a reporter moiety or an internal standard reporter protein, the fluorescence values were quantitatively analyzed by a fluorescence meter. When the reporter moiety is mCherry and the internal standard reporter protein is eGFP, mCherry was excited at a wavelength of 610 nm and emitted light at a wavelength of 507 nm was measured by using SpectraMax (Molecular Device), a fluorescence meter. For eGFP, eGFP was excited at the wavelength of 488 nm and emitted light at a wavelength of 507 nm was measured. Normalization was performed by using a resultant value obtained by dividing the measured mCherry emission value by the internal standard reporter protein eGFP emission value. In addition, fluorescence values of GFP and RFP may be measured by using an Incucyte device (Essen Bioscience Inc.) to perform normalization. eGFP belongs to a GFP family and mCherry belongs to an RFP family.

(6) Results

FIG. 5 shows measurements of activities of a reporter moiety after NG108-15 cells transfected with pFB vector 1 were differentiated into neurons and then intoxicated with *botulinum* toxin A. Referring to FIG. 5, production of NG108-15 cells transfected with pFB vector 1, differentiation into neurons, intoxication with *botulinum* toxin A, and measurement of reporter moiety activity are the same as described in (3), (4), and (5). Referring to FIG. 5, to measure the activity of nano-luciferase, luminescence of the cells that had been cultured for being intoxicated for the total of 72 hours were measured by using the Nano-luciferase kit. As shown in FIG. 5, the measured activity of the nano-luciferase, which was evaluated by relative luminescence unit, was significantly increased when the cells were intoxicated with 10 nM *botulinum* toxin A compared with when not intoxicated therewith.

Figure 6:
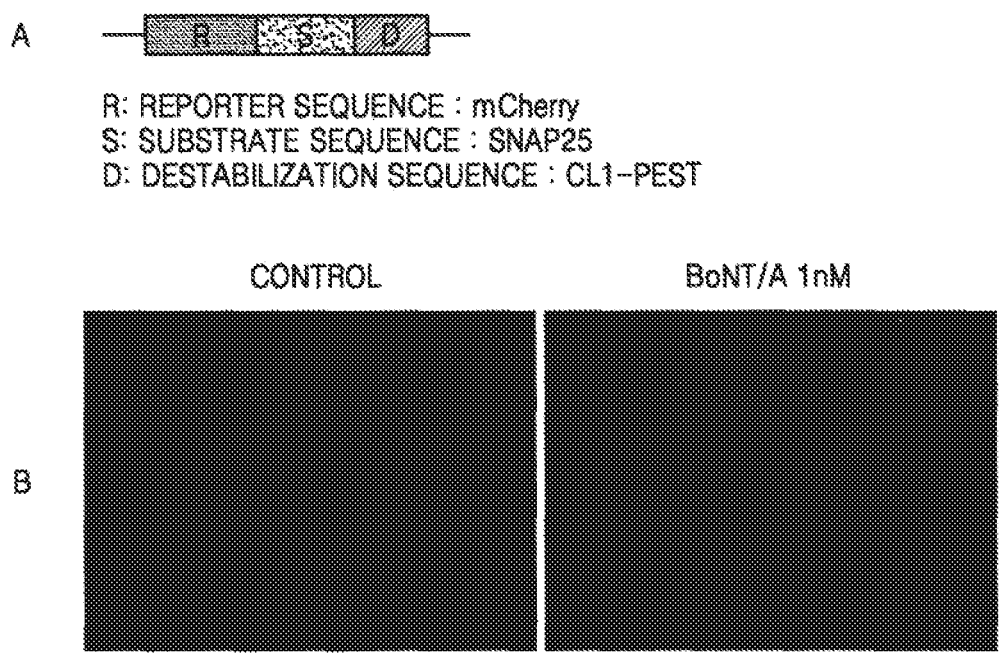
FIG. 6 shows fluorescent microscopic images of NG108-15 cells transfected with pFB vector 2 after the cells were differentiated into neurons and then intoxicated with *botulinum* toxin A.

FIG. 6 shows fluorescent microscopic images of NG108-15 cells transfected with pFB vector 2 after the cells were differentiated into neurons and then intoxicated with *botulinum* toxin A. Referring to FIG. 6, the production of NG108-15 cells transfected with pFB vector 2, differentiation into neurons, and intoxication with *botulinum* toxin A are the same as described in (3) and (4). FIG. 6 shows fluorescence images of cells, cultured for the total of 72 hours for intoxication, obtained by using an Olympus FSX-100 device, which is a fuorescence microscope.

Referring to FIG. 6, Control is of a control group with 0 nM of a *botulinum* toxin A, and BoNT/A 1 nM is of a test group with 1 nM of a *botulinum* toxin A. As shown in FIG. 6, the test group showed a significant increase in the number of cells with red fluorescence.

FIGS. 5 and 6 show that when the cleavage site of SNAP25 is not cleaved by *botulinum* toxin A, the polypeptides of the NLuc-SNPA25 substrate moiety-CL1-PEST structure are easily degraded and the relative luminescent unit is low, and when the cleavage site of SNAP25 is cleaved by *botulinum* toxin A, the polypeptides of the NLuc-SNPA25 substrate moiety-CL1-PEST structure is stabilized from degradation, and the relative luminescent unit is high.

Figure 7:
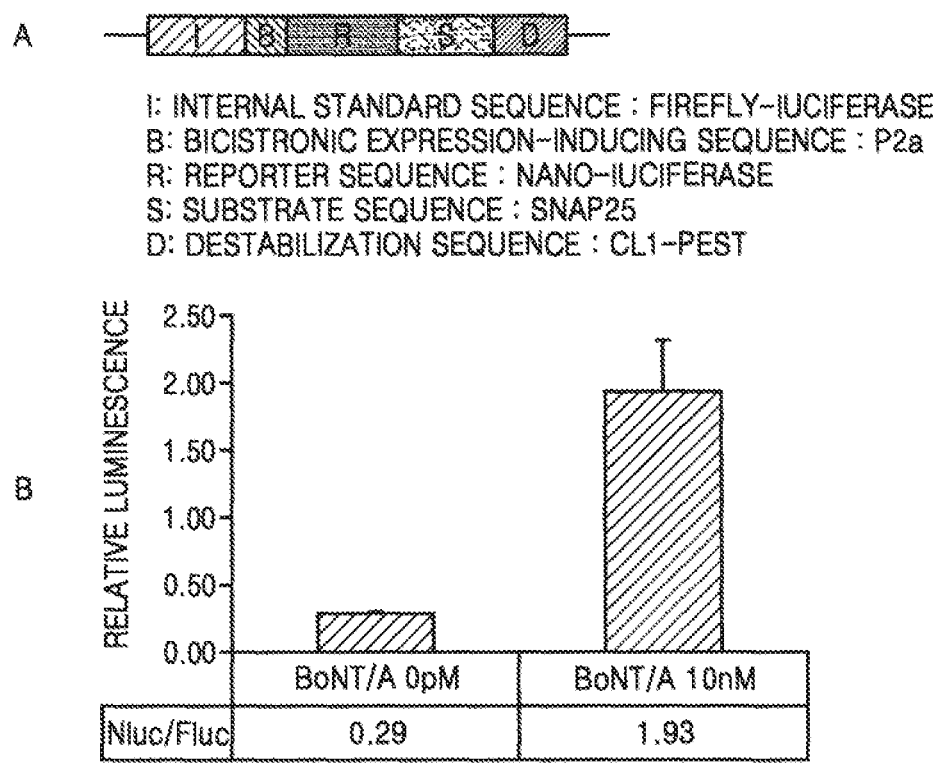
FIG. 7 shows measurements of activities of a reporter moiety of NG108-15 cells transfected with pFB vector 3 after the cells were differentiated into neurons and then intoxicated with *botulinum* toxin A.

FIG. 7 shows fluorescent microscopic images of NG108-15 cells transfected with pFB vector 3 after the cells were differentiated into neurons and then intoxicated with *botulinum* toxin A. Referring to FIG. 7, production of NG108-15 cells transfected with pFB vector 3, differentiation into neurons, intoxication with *botulinum* toxin A, and measurement of reporter moiety activity are the same as described in (3), (4), and (5). Referring to FIG. 7, the activities of FLuc and NLuc were measured by measuring the luminescence of the cells cultured for intoxication for the total of 72 hours by using a One-glo nano dual luciferase kit.

As shown in FIG. 7, the relative activity of NLuc with respect to FLuc, which was evaluated by a relative luminescence unit, was significantly increased when the cells were intoxicated with 10 nM *botulinum* toxin A compared to when not intoxicated therewith. Referring to FIG. 6, BoNT/A is of a control group with 0 nM of a *botulinum* toxin A, and BoNT/A 1 nM is of a test group with 1 nM of a *botulinum* toxin A. As shown in FIG. 7, the measured activity of NLuc, which was evaluated by relative luminescence, was significantly increased when the cells were intoxicated with 10 nM *botulinum* toxin A compared with when not intoxicated therewith.

Figure 8:
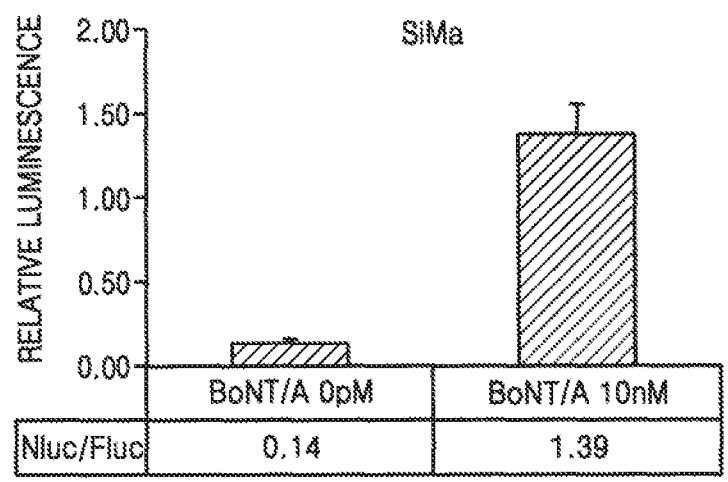
FIG. 8 shows measurements of activities of a reporter moiety of SiMa cells transfected with pFB vector 3 after the cells were differentiated into neurons and then intoxicated with *botulinum* toxin A.

FIG. 8 shows fluorescent microscopic images of SiMa cells transfected with pFB vector 3 after the cells were differentiated into neurons and then intoxicated with *botulinum* toxin A.

Figure 9:
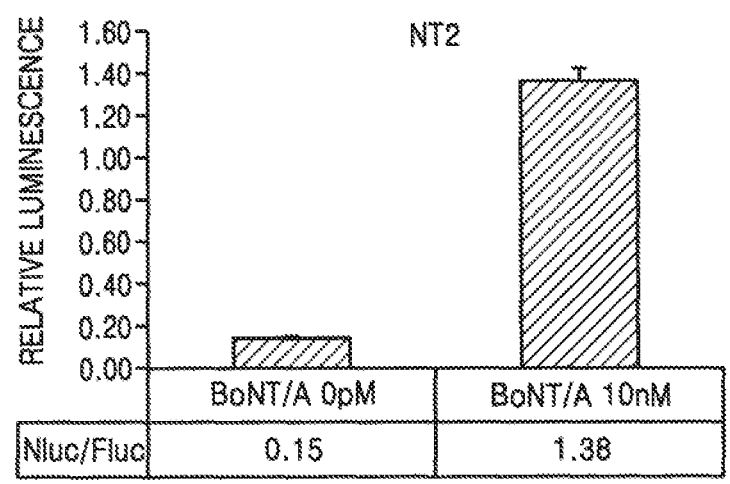
FIG. 9 shows measurements of activities of a reporter moiety of NT2 cells transfected with pFB vector 3 after the cells were differentiated into neurons and then intoxicated with *botulinum* toxin A.

FIG. 9 shows fluorescent microscopic images of NT2 cells transfected with pFB vector 3 after the cells were differentiated into neurons and then intoxicated with *botulinum* toxin A.

FIGS. 8 and 9 show results obtained in the same manner as used to obtain results shown in FIG. 7, except that SiMa cells and NT2 cells were used instead of NG108-15 cells. As shown in FIGS. 8 and 9, the measured activity of NLuc, which was evaluated by relative luminescence, was significantly increased when the cells were intoxicated with 10 nM *botulinum* toxin A compared with when not intoxicated therewith.

FIG. 10 shows measurements of signals emitted by a reporter moiety protein and an internal standard reporter protein expressed after light chain of BoNT/B (pCDNA4-BLC) was arbitrarily expressed in NG108-15 cells that were induced to be transfected by using pFB vector 4 to stably express a polypeptide. Here, regarding the pCDNA4-BLC vector, Lipofectamine™ 3000 (Invitrogen) was used and transduction was performed according to the manufacturer's instructions. Cells were cultured under the same conditions for 48 hours after the transduction. Accordingly, the pCDNA4-BLC vector is transiently expressed in NG108-15 cells. In FIG. 10, the vertical axis indicates values obtained by normalizing NLuc values with respect to Flue.

As shown in FIG. 10, the activity of NLuc measured with respect to FLuc, which was evaluated by relative luminescence, was significantly increased when DNA of pCDNA4-BLC encoding the light chain of 10 μg *botulinum* toxin B was introduced compared to when not introduced.

FIG. 11 shows measurements of signals emitted by a reporter moiety protein after cell line NT2 cells transducted with pFB vector 3 and stabilized were intoxicated with a different concentration of BoNT/A. In FIG. 11, BoNT/A API represents an active pharmaceutical ingredient used to manufacture a product containing BoNT/A. Herein, the active pharmaceutical ingredient is used as BoNT/A. BoNT/A API was supplied by Meditox Co., Ltd. pFB vector 3 was transduced by using Lipofectamine™ 3000 (Invitrogen) according to the manufacturer's instructions. Cells were cultured under the same conditions for 48 hours after the transduction. Accordingly, pFB vector 3 is transiently expressed in NT2 cells. In FIG. 11, RLU represents a relative luciferase unit. As shown in FIG. 11, the activity of NLuc measured with respect to the FLuc, which was evaluated by relative luminescence unit, is dependent on the concentration of *botulinum* toxin A at the concentration of 1 pM to 10 nM. This indicates that by measuring RLU, the level of the *botulinum* toxin in a sample, for example, the level of type A, may be measured.

Figure 13:
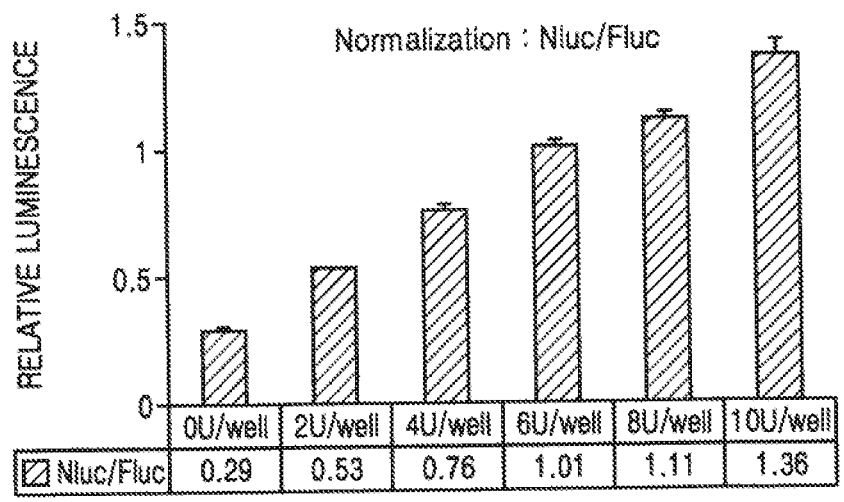
Figure 14:
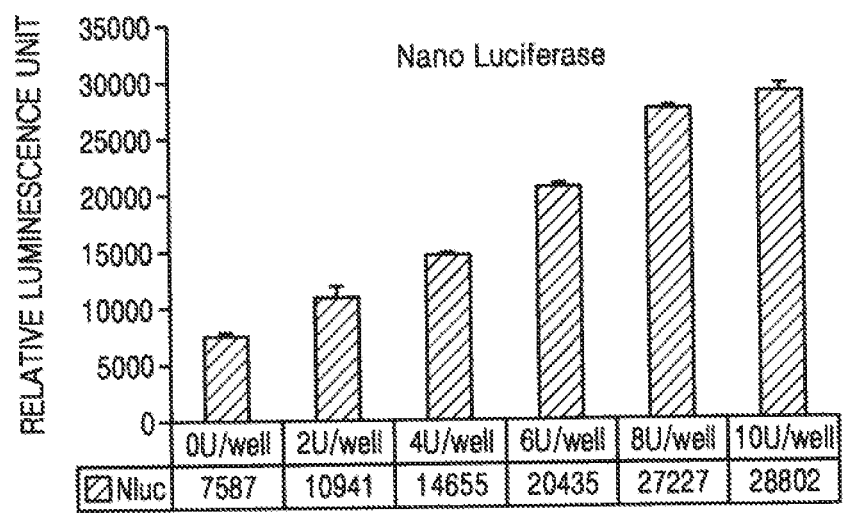

FIGS. 12 to 14 show measurements of signals emitted by a reporter moiety and an internal standard reporter protein expressed in NT2 cells that were transfected with pFB vector 3 and stabilized after the cells were intoxicated with different concentrations of BoNT/A-containing final products. Results shown in FIGS. 12 to 14 were obtained in the same manner as described in connection with FIG. 11, except that as BoNT/A, a final product containing BoNT/A was used instead of a active pharmaceutical ingredient used to produce a product containing BoNT/A. Compared to BoNT/A API, the product further contains ingredients such as excipients. FIGS. 12, 13, and 14 show FLuc values, NLuc values, and NLuc/FLuc values, respectively.

As shown in FIG. 14, the activity of NLuc with respect to FLuc, which was evaluated by relative luminescence unit, was dependent on the concentration of *botulinum* toxin A at a concentration of 1 U to 10 U. This indicates that by measuring RLU, the level of the *botulinum* toxin in a sample, for example, the level of type A, may be measured.

INDUSTRIAL APPLICABILITY

The recombinant polynucleotide according to the first aspect may be used to determine protease activities of a neurotoxin polypeptide in a host cell or sample containing the recombinant polynucleotide.

The host cell containing the recombinant polynucleotide according to the second aspect may be efficiently used in determining protease activities of a neurotoxin polypeptide in a sample.

The kit for determining proteolytic activities of a neurotoxin polypeptide according to the third and fourth aspects may be used to determine proteolytic activities of a neurotoxin polypeptide.

According to the method of determining characteristics of a neurotoxin polypeptide in a sample according to the fifth and seventh aspects, characteristics of a neurotoxin polypeptide may be efficiently determined.

According to the method of determining characteristics of a neurotoxin polypeptide in a sample according to the sixth and eighth aspects, protease activities of a neurotoxin polypeptide in a sample may be efficiently determined.

According to the method of measuring the ability of a host cell to express or inhibit a protease according to the ninth aspect, the ability of a host cell to express or inhibit a protease may be efficiently measured or it may be determined whether a test material controls protease activities.

The invention claimed is:

1. A recombinant polynucleotide comprising a polynucleotide that encodes a polypeptide comprising from N- to C-terminus, a reporter moiety, a substrate moiety comprising a protease cleavage site, and a destabilization moiety, wherein said protease cleavage site is capable of being cleaved by a neurotoxin polypeptide.

2. The recombinant polynucleotide of claim 1, wherein the neurotoxin polypeptide is *botulinum* toxin serotype A (BoNT/A), BoNT/B, BoNT/C, BoNT/CD, BoNT/D, BoNT/DC, BoNT/E, BoNT/F, BoNT/FA, BoNT/G, or tetanus neurotoxin (TeNT).

3. The recombinant polynucleotide of claim 1, further comprising a second polynucleotide encoding a bicistronic sequence linked upstream of the polynucleotide and an internal standard reporter operably linked upstream of the bicistronic sequence or a second polynucleotide encoding a bicistronic sequence linked downstream of the polynucleotide and an internal standard reporter operably linked downstream of the bicistronic sequence.

4. The recombinant polynucleotide of claim 3, wherein the bicistronic sequence is an internal ribosomal entry site (IRES) sequence or a nucleotide sequence that allows ribosome to skip forming a peptide bond.

5. A host cell containing the recombinant polynucleotide of claim 1, wherein the host cell is a cell that is capable of translocating a neurotoxin polypeptide capable of cleaving the protease cleavage site into a cytoplasm.

6. The host cell of claim 5, wherein the host cell is a NT2 cell, SiMa cell, or NG108-15 cell.

7. A host cell containing the recombinant polynucleotide of claim 1, wherein the host cell further comprises an exogenous polynucleotide encoding a neurotoxin polypeptide capable of cleaving the protease cleavage site.

8. A host cell containing the recombinant polynucleotide of claim 3, wherein the host cell is a cell that is capable of translocating a neurotoxin polypeptide into a cytoplasm.

9. The host cell of claim 8, wherein the host cell is NT2 cell, SiMa cell, or NG108-15 cell.

10. A host cell containing the recombinant polynucleotide of claim 3, wherein the host cell further comprises an exogenous polynucleotide encoding a neurotoxin polypeptide capable of cleaving the protease cleavage site.

11. The host cell of claim 10, wherein the host cell is NT2 cell, SiMa cell, or NG108-15 cell.

12. A method of determining proteolytic activities of a neurotoxin polypeptide in a sample, the method comprising:
   contacting the host cell of claim 5 with a sample suspected of containing a neurotoxin polypeptide capable of cleaving the protease cleavage site; and
   measuring a signal emitted by the reporter moiety in a product obtained by the contacting.

13. A method of determining proteolytic activities of a neurotoxin polypeptide in a sample, the method comprising:
   contacting the host cell of claim 8 with a sample suspected of containing a neurotoxin polypeptide capable of cleaving the protease cleavage site; and
   measuring a signal emitted by the reporter moiety in a product obtained by the contacting.

14. A method of measuring the ability of a candidate test material to alter the activity of a neurotoxin polypeptide protease, said method comprising:
   culturing the host cell of claim 7 in the presence of the candidate test material; and
   measuring signals emitted by the reporter moiety in a culture,
   wherein the candidate test material does not inhibit the neurotoxin polypeptide protease when the reporter moiety emits a signal.

15. A method of measuring the ability of a candidate test material to alter the activity of a neurotoxin polypeptide protease, said method comprising:
   culturing the host cell of claim 10 in the presence of the candidate test material; and
   measuring signals emitted by the reporter moiety in a culture,
   wherein the candidate test material does not inhibit the neurotoxin polypeptide protease when the reporter moiety emits a signal.

* * * * *

SEQUENCE LISTING

<160> NUMBER OF SEQ ID NOS: 24

<210> SEQ ID NO 1
<211> LENGTH: 1653
<212> TYPE: DNA
<213> ORGANISM: Firefly

<400> SEQUENCE: 1

| | | | | | |
|---|---|---|---|---|---|
| atggaagatg | ccaaaaacat | taagaagggc | ccagcgccat | tctacccact | cgaagacggg | 60 |
| accgccggcg | agcagctgca | caaagccatg | aagcgctacg | ccctggtgcc | cggcaccatc | 120 |
| gcctttaccg | acgcacatat | cgaggtggac | attacctacg | ccgagtactt | cgagatgagc | 180 |
| gttcggctgg | cagaagctat | gaagcgctat | gggctgaata | caaaccatcg | gatcgtggtg | 240 |
| tgcagcgaga | atagcttgca | gttcttcatg | cccgtgttgg | gtgccctgtt | catcggtgtg | 300 |
| gctgtggccc | cagctaacga | catctacaac | gagcgcgagc | tgctgaacag | catgggcatc | 360 |
| agccagccca | ccgtcgtatt | cgtgagcaag | aaagggctgc | aaaagatcct | caacgtgcaa | 420 |
| aagaagctac | cgatcataca | aaagatcatc | atcatggata | gcaagaccga | ctaccagggc | 480 |
| ttccaaagca | tgtacacctt | cgtgacttcc | catttgccac | ccggcttcaa | cgagtacgac | 540 |
| ttcgtgcccg | agagcttcga | ccgggacaaa | accatcgccc | tgatcatgaa | cagtagtggc | 600 |
| agtaccggat | tgcccaaggg | cgtagcccta | ccgcaccgca | ccgcttgtgt | ccgattcagt | 660 |
| catgcccgcg | accccatctt | cggcaaccag | atcatccccg | acaccgctat | cctcagcgtg | 720 |
| gtgccatttc | accacggctt | cggcatgttc | accacgctgg | gctacttgat | ctgcggcttt | 780 |
| cgggtcgtgc | tcatgtaccg | cttcgaggag | gagctattct | tgcgcagctt | gcaagactat | 840 |
| aagattcaat | ctgccctgct | ggtgcccaca | ctatttagct | tcttcgctaa | gagcactctc | 900 |
| atcgacaagt | acgacctaag | caacttgcac | gagatcgcca | gcggcggggc | cgcgctcagc | 960 |
| aaggaggtag | gtgaggccgt | ggccaaacgc | ttccacctac | caggcatccg | ccagggctac | 1020 |
| ggcctgacag | aaacaaccag | cgccattctg | atcacccccg | aaggggacga | caagcctggc | 1080 |
| gcagtaggca | aggtggtgcc | cttcttcgag | gctaaggtgg | tggacttgga | caccggtaag | 1140 |
| acactgggtg | tgaaccagcg | cggcgagctg | tgcgtccgtg | gccccatgat | catgagcggc | 1200 |
| tacgttaaca | accccgaggc | tacaaacgct | ctcatcgaca | aggacggctg | gctgcacagc | 1260 |
| ggcgacatcg | cctactggga | cgaggacgag | cacttcttca | tcgtggaccg | gctgaagagc | 1320 |
| ctgatcaaat | acaagggcta | ccaggtagcc | ccagccgaac | tggagagcat | cctgctgcaa | 1380 |
| caccccaaca | tcttcgacgc | cggggtcgcc | ggcctgcccg | acgacgatgc | cggcgagctg | 1440 |
| cccgccgcag | tcgtcgtgct | ggaacacggt | aaaaccatga | ccgagaagga | gatcgtggac | 1500 |
| tatgtggcca | gccaggttac | aaccgccaag | aagctgcgcg | gtggtgttgt | gttcgtggac | 1560 |
| gaggtgccta | aggactgac | cggcaagttg | gacgcccgca | agatccgcga | gattctcatt | 1620 |
| aaggccaaga | agggcggcaa | gatcgccgtg | tga | | | 1653 |

<210> SEQ ID NO 2
<211> LENGTH: 516
<212> TYPE: DNA
<213> ORGANISM: Artificial Sequence
<220> FEATURE:
<223> OTHER INFORMATION: Nano-luciferase

<400> SEQUENCE: 2

| | | | | | |
|---|---|---|---|---|---|
| atggtcttca | cactcgaaga | tttcgttggg | gactggcgac | agacagccgg | ctacaacctg | 60 |
| gaccaagtcc | ttgaacaggg | aggtgtgtcc | agtttgtttc | agaatctcgg | ggtgtccgta | 120 |

| | |
|---|---|
| actccgatcc aaaggattgt cctgagcggt gaaaatgggc tgaagatcga catccatgtc | 180 |
| atcatcccgt atgaaggtct gagcggcgac caaatgggcc agatcgaaaa aatttttaag | 240 |
| gtggtgtacc ctgtggatga tcatcacttt aaggtgatcc tgcactatgg cacactggta | 300 |
| atcgacgggg ttacgccgaa catgatcgac tatttcggac ggccgtatga aggcatcgcc | 360 |
| gtgttcgacg gcaaaaagat cactgtaaca gggaccctgt ggaacggcaa caaaattatc | 420 |
| gacgagcgcc tgatcaaccc cgacggctcc ctgctgttcc gagtaaccat caacggagtg | 480 |
| accggctggc ggctgtgcga acgcattctg gcgtga | 516 |

<210> SEQ ID NO 3
<211> LENGTH: 720
<212> TYPE: DNA
<213> ORGANISM: Artificial Sequence
<220> FEATURE:
<223> OTHER INFORMATION: Enhanced GFP

<400> SEQUENCE: 3

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgaccta cggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaagtga | 720 |

<210> SEQ ID NO 4
<211> LENGTH: 711
<212> TYPE: DNA
<213> ORGANISM: Artificial Sequence
<220> FEATURE:
<223> OTHER INFORMATION: mCherry

<400> SEQUENCE: 4

| | |
|---|---|
| atggtgagca agggcgagga ggataacatg gccatcatca aggagttcat gcgcttcaag | 60 |
| gtgcacatgg agggctccgt gaacggccac gagttcgaga tcgagggcga gggcgagggc | 120 |
| cgcccctacg agggcaccca gaccgccaag ctgaaggtga ccaagggtgg ccccctgccc | 180 |
| ttcgcctggg acatcctgtc ccctcagttc atgtacggct ccaaggccta cgtgaagcac | 240 |
| cccgccgaca tccccgacta cttgaagctg tccttccccg agggcttcaa gtgggagcgc | 300 |
| gtgatgaact tcgaggacgg cggcgtggtg accgtgaccc aggactcctc cctgcaggac | 360 |
| ggcgagttca tctacaaggt gaagctgcgc ggcaccaact tcccctccga cggccccgta | 420 |
| atgcagaaga agaccatggg ctgggaggcc tcctccgagc ggatgtaccc cgaggacggc | 480 |
| gccctgaagg gcgagatcaa gcagaggctg aagctgaagg acggcggcca ctacgacgct | 540 |
| gaggtcaaga ccacctacaa ggccaagaag cccgtgcagc tgcccggcgc ctacaacgtc | 600 |

```
aacatcaagt tggacatcac ctcccacaac gaggactaca ccatcgtgga acagtacgaa      660
cgcgccgagg ccgccactc caccggcggc atggacgagc tgtacaagtg a                711
```

<210> SEQ ID NO 5
<211> LENGTH: 66
<212> TYPE: DNA
<213> ORGANISM: Artificial Sequence
<220> FEATURE:
<223> OTHER INFORMATION: P2A

<400> SEQUENCE: 5

```
ggaagcggag ctactaactt cagcctgctg aagcaggctg agacgtgga ggagaaccct       60 ggacct                                                                 66
```

<210> SEQ ID NO 6
<211> LENGTH: 186
<212> TYPE: DNA
<213> ORGANISM: Artificial Sequence
<220> FEATURE:
<223> OTHER INFORMATION: partial SNAP25

<400> SEQUENCE: 6

```
gagatggatg agaacctgga gcaggtgagc ggcatcatcg aaacctccg ccatatggct       60 ctagacatgg gcaatgagat tgacacccag aatcgccaga tcgacaggat catggagaag     120
gctgattcca acaaaaccag aattgatgaa gccaaccaac gtgcaacaaa gatgctggga     180
agtggt                                                                186
```

<210> SEQ ID NO 7
<211> LENGTH: 48
<212> TYPE: DNA
<213> ORGANISM: Artificial Sequence
<220> FEATURE:
<223> OTHER INFORMATION: CL1

<400> SEQUENCE: 7

```
gcttgcaaga actggttcag tagcttaagc cactttgtga tccacctt                   48
```

<210> SEQ ID NO 8
<211> LENGTH: 120
<212> TYPE: DNA
<213> ORGANISM: Artificial Sequence
<220> FEATURE:
<223> OTHER INFORMATION: PEST

<400> SEQUENCE: 8

```
agccacggct tccctcccga ggtggaggag caggccgccg gcaccctgcc catgagctgc      60
gcccaggaga gcggcatgga tagacaccct gctgcttgcg ccagcgccag gatcaacgtc     120
```

<210> SEQ ID NO 9
<211> LENGTH: 550
<212> TYPE: PRT
<213> ORGANISM: Artificial Sequence
<220> FEATURE:
<223> OTHER INFORMATION: Firefly luciferase

<400> SEQUENCE: 9

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
```

```
              35                  40                  45
Val Asp Ile Thr Tyr Ala Glu Tyr Phe Glu Met Ser Val Arg Leu Ala
 50                  55                  60

Glu Ala Met Lys Arg Tyr Gly Leu Asn Thr Asn His Arg Ile Val Val
 65                  70                  75                  80

Cys Ser Glu Asn Ser Leu Gln Phe Phe Met Pro Val Leu Gly Ala Leu
                     85                  90                  95

Phe Ile Gly Val Ala Val Ala Pro Ala Asn Asp Ile Tyr Asn Glu Arg
                100                 105                 110

Glu Leu Leu Asn Ser Met Gly Ile Ser Gln Pro Thr Val Val Phe Val
                115                 120                 125

Ser Lys Lys Gly Leu Gln Lys Ile Leu Asn Val Gln Lys Lys Leu Pro
130                 135                 140

Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
                180                 185                 190

Ala Leu Ile Met Asn Ser Ser Gly Ser Thr Gly Leu Pro Lys Gly Val
                195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
                260                 265                 270

Phe Leu Arg Ser Leu Gln Asp Tyr Lys Ile Gln Ser Ala Leu Leu Val
                275                 280                 285

Pro Thr Leu Phe Ser Phe Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
                340                 345                 350

Pro Glu Gly Asp Asp Lys Pro Gly Ala Val Gly Lys Val Val Pro Phe
                355                 360                 365

Phe Glu Ala Lys Val Val Asp Leu Asp Thr Gly Lys Thr Leu Gly Val
                370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
                420                 425                 430

Phe Ile Val Asp Arg Leu Lys Ser Leu Ile Lys Tyr Lys Gly Tyr Gln
                435                 440                 445

Val Ala Pro Ala Glu Leu Glu Ser Ile Leu Leu Gln His Pro Asn Ile
                450                 455                 460
```

Phe Asp Ala Gly Val Ala Gly Leu Pro Asp Asp Ala Gly Glu Leu
465                 470                 475                 480

Pro Ala Ala Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
530                 535                 540

Gly Gly Lys Ile Ala Val
545                 550

<210> SEQ ID NO 10
<211> LENGTH: 171
<212> TYPE: PRT
<213> ORGANISM: Artificial Sequence
<220> FEATURE:
<223> OTHER INFORMATION: Nano-luciferase

<400> SEQUENCE: 10

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170

<210> SEQ ID NO 11
<211> LENGTH: 239
<212> TYPE: PRT
<213> ORGANISM: Artificial Sequence
<220> FEATURE:
<223> OTHER INFORMATION: Enhanced GFP

<400> SEQUENCE: 11

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile

```
            35                  40                  45
Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 12
<211> LENGTH: 236
<212> TYPE: PRT
<213> ORGANISM: Artificial Sequence
<220> FEATURE:
<223> OTHER INFORMATION: mCherry

<400> SEQUENCE: 12

Met Val Ser Lys Gly Glu Glu Asp Asn Met Ala Ile Ile Lys Glu Phe
 1               5                  10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
 50                  55                  60

Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
```

```
                165                 170                 175
His Tyr Asp Ala Glu Val Lys Thr Thr Tyr Lys Ala Lys Lys Pro Val
            180                 185                 190
Gln Leu Pro Gly Ala Tyr Asn Val Asn Ile Lys Leu Asp Ile Thr Ser
        195                 200                 205
His Asn Glu Asp Tyr Thr Ile Val Glu Gln Tyr Arg Ala Glu Gly
    210                 215                 220
Arg His Ser Thr Gly Gly Met Asp Glu Leu Tyr Lys
225                 230                 235

<210> SEQ ID NO 13
<211> LENGTH: 22
<212> TYPE: PRT
<213> ORGANISM: Artificial Sequence
<220> FEATURE:
<223> OTHER INFORMATION: P2A

<400> SEQUENCE: 13

Gly Ser Gly Ala Thr Asn Phe Ser Leu Leu Lys Gln Ala Gly Asp Val
1               5                   10                  15
Glu Glu Asn Pro Gly Pro
            20

<210> SEQ ID NO 14
<211> LENGTH: 62
<212> TYPE: PRT
<213> ORGANISM: Artificial Sequence
<220> FEATURE:
<223> OTHER INFORMATION: partial SNAP25

<400> SEQUENCE: 14

Glu Met Asp Glu Asn Leu Glu Gln Val Ser Gly Ile Ile Gly Asn Leu
1               5                   10                  15
Arg His Met Ala Leu Asp Met Gly Asn Glu Ile Asp Thr Gln Asn Arg
            20                  25                  30
Gln Ile Asp Arg Ile Met Glu Lys Ala Asp Ser Asn Lys Thr Arg Ile
        35                  40                  45
Asp Glu Ala Asn Gln Arg Ala Thr Lys Met Leu Gly Ser Gly
    50                  55                  60

<210> SEQ ID NO 15
<211> LENGTH: 16
<212> TYPE: PRT
<213> ORGANISM: Artificial Sequence
<220> FEATURE:
<223> OTHER INFORMATION: CL1

<400> SEQUENCE: 15

Ala Cys Lys Asn Trp Phe Ser Ser Leu Ser His Phe Val Ile His Leu
1               5                   10                  15

<210> SEQ ID NO 16
<211> LENGTH: 40
<212> TYPE: PRT
<213> ORGANISM: Artificial Sequence
<220> FEATURE:
<223> OTHER INFORMATION: PEST

<400> SEQUENCE: 16

Ser His Gly Phe Pro Pro Glu Val Glu Glu Gln Ala Ala Gly Thr Leu
1               5                   10                  15
Pro Met Ser Cys Ala Gln Glu Ser Gly Met Asp Arg His Pro Ala Ala
```

Cys Ala Ser Ala Arg Ile Asn Val
        35                  40

<210> SEQ ID NO 17
<211> LENGTH: 345
<212> TYPE: DNA
<213> ORGANISM: Artificial Sequence
<220> FEATURE:
<223> OTHER INFORMATION: Vamp

<400> SEQUENCE: 17

```
atgtcggcta ccgctgccac cgtcctgcct gccgccccgg ccggcgaggg tggcccccct    60
gcacctcctc caaaccttac tagtaacagg agactgcagc agacgcaggc ccaggtggat   120
gaggtggtgg acatcatgag ggtgaatgtg gacaaggtcc tggagcggga ccagaagttg   180
tcggagctgg atgaccgtgc agatgccctc caggcagggg cctcccagtt tgaaacaagt   240
gcagccaagc tcaagcgcaa atactggtgg aaaaacctca agatgatgat catcttggga   300
gtgatctgcg ccatcatcct catcatcatc atcgtttact tcagc                   345
```

<210> SEQ ID NO 18
<211> LENGTH: 115
<212> TYPE: PRT
<213> ORGANISM: Artificial Sequence
<220> FEATURE:
<223> OTHER INFORMATION: Vamp

<400> SEQUENCE: 18

Met Ser Ala Thr Ala Ala Thr Val Leu Pro Ala Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser
        115

<210> SEQ ID NO 19
<211> LENGTH: 63
<212> TYPE: DNA
<213> ORGANISM: Artificial Sequence
<220> FEATURE:
<223> OTHER INFORMATION: T2A

<400> SEQUENCE: 19

```
ggaaccggag agggcagagg aagtctgcta acatgcgctg acgtcgagga gaatcctgga    60
cct                                                                  63
```

<210> SEQ ID NO 20
<211> LENGTH: 21
<212> TYPE: PRT

<213> ORGANISM: Artificial Sequence
<220> FEATURE:
<223> OTHER INFORMATION: T2A

<400> SEQUENCE: 20

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 21
<211> LENGTH: 69
<212> TYPE: DNA
<213> ORGANISM: Artificial Sequence
<220> FEATURE:
<223> OTHER INFORMATION: E2A

<400> SEQUENCE: 21
ggaagcggac agtgtactaa ttatgctctc ttgaaattgg ctggagatgt tgagagcaac    60
cctggacct                                                           69

<210> SEQ ID NO 22
<211> LENGTH: 23
<212> TYPE: PRT
<213> ORGANISM: Artificial Sequence
<220> FEATURE:
<223> OTHER INFORMATION: E2A

<400> SEQUENCE: 22

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 23
<211> LENGTH: 75
<212> TYPE: DNA
<213> ORGANISM: Artificial Sequence
<220> FEATURE:
<223> OTHER INFORMATION: F2A

<400> SEQUENCE: 23
ggaagcggag tgaaacagac tttgaatttt gaccttctca gttggcggg agacgtggag     60 tgcaaccctg gacct                                                    75

<210> SEQ ID NO 24
<211> LENGTH: 25
<212> TYPE: PRT
<213> ORGANISM: Artificial Sequence
<220> FEATURE:
<223> OTHER INFORMATION: F2A

<400> SEQUENCE: 24

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25